US009861570B2

(12) United States Patent
Gurtner et al.

(10) Patent No.: US 9,861,570 B2
(45) Date of Patent: *Jan. 9, 2018

(54) THREADS OF HYALURONIC ACID AND/OR DERIVATIVES THEREOF, METHODS OF MAKING THEREOF AND USES THEREOF

(71) Applicant: Allergan Holdings France S.A.S., Courbevoie (FR)

(72) Inventors: Geoffrey C. Gurtner, Stanford, CA (US); Kenneth N. Horne, San Francisco, CA (US); Jayakumar Rajadas, Cupertino, CA (US)

(73) Assignee: Allergan Holdings France S.A.S., Courbevoie (FR)

(*) Notice: Subject to any disclaimer, the term of this patent is extended or adjusted under 35 U.S.C. 154(b) by 0 days.

This patent is subject to a terminal disclaimer.

(21) Appl. No.: 14/947,409

(22) Filed: Nov. 20, 2015

(65) Prior Publication Data

US 2016/0074307 A1    Mar. 17, 2016

Related U.S. Application Data

(63) Continuation of application No. 13/060,919, filed as application No. PCT/US2009/055704 on Sep. 2, 2009, now Pat. No. 9,228,027.
(Continued)

(51) Int. Cl.
*A61L 31/04* (2006.01)
*A61L 27/20* (2006.01)
(Continued)

(52) U.S. Cl.
CPC .............. *A61K 8/735* (2013.01); *A61K 8/027* (2013.01); *A61K 8/0216* (2013.01); *A61K 8/42* (2013.01); *A61K 8/65* (2013.01); *A61L 15/28* (2013.01); *A61L 17/005* (2013.01); *A61L 17/04* (2013.01); *A61L 17/06* (2013.01); *A61L 17/10* (2013.01);
(Continued)

(58) Field of Classification Search
None
See application file for complete search history.

(56) References Cited

U.S. PATENT DOCUMENTS

| 1,558,037 | A | 10/1925 | Morton |
| 1,960,117 | A | 5/1934 | Lydeard |

(Continued)

FOREIGN PATENT DOCUMENTS

| CA | 0949965 A1 | 6/1974 |
| CA | 104144714 A | 11/2014 |

(Continued)

OTHER PUBLICATIONS

Adams, Mark, An Analysis of Clinical Studies of the Use of Crosslinked Hyaluronan, Hylan, in the Treatment of Osteoarthritis, The Journal of Rheumatology, 1993, 16-18, 20 (39).
(Continued)

*Primary Examiner* — Theodore R. West
(74) *Attorney, Agent, or Firm* — Linda Allyson Nassif

(57) ABSTRACT

The present invention provides threads of hyaluronic acid, and/or derivatives thereof, methods of making thereof and uses thereof, for example, in aesthetic applications (e.g., dermal fillers), surgery (sutures), drug delivery, etc.

5 Claims, 12 Drawing Sheets

Related U.S. Application Data

(60) Provisional application No. 61/190,866, filed on Sep. 2, 2008.

(51) Int. Cl.

| | | |
|---|---|---|
| *A61Q 19/08* | (2006.01) | |
| *C08L 5/08* | (2006.01) | |
| *A61K 8/73* | (2006.01) | |
| *A61L 15/28* | (2006.01) | |
| *A61L 17/06* | (2006.01) | |
| *C08B 37/08* | (2006.01) | |
| *A61K 8/02* | (2006.01) | |
| *A61K 8/42* | (2006.01) | |
| *A61L 17/00* | (2006.01) | |
| *A61L 17/04* | (2006.01) | |
| *A61L 27/54* | (2006.01) | |
| *A61K 8/65* | (2006.01) | |
| *A61L 17/10* | (2006.01) | |

(52) U.S. Cl.
CPC ............... *A61L 27/20* (2013.01); *A61L 27/54* (2013.01); *A61L 31/042* (2013.01); *A61Q 19/08* (2013.01); *C08B 37/0072* (2013.01); *C08L 5/08* (2013.01); *A61K 2800/805* (2013.01); *A61L 2300/402* (2013.01); *A61L 2430/34* (2013.01); *C08L 2205/025* (2013.01); *Y10T 428/2929* (2015.01)

(56) References Cited

U.S. PATENT DOCUMENTS

| | | |
|---|---|---|
| 2,128,827 A | 8/1938 | Killian |
| 3,548,056 A | 12/1970 | Eigen |
| 3,611,551 A | 10/1971 | Shave et al. |
| 3,763,009 A | 10/1973 | Suzuki et al. |
| 3,949,073 A | 4/1976 | Daniels et al. |
| 4,060,081 A | 11/1977 | Yannas et al. |
| 4,140,537 A | 2/1979 | Luck et al. |
| 4,233,360 A | 11/1980 | Luck et al. |
| 4,273,705 A | 6/1981 | Kato |
| 4,279,812 A | 7/1981 | Cioca |
| 4,424,208 A | 1/1984 | Wallace et al. |
| 4,500,676 A | 2/1985 | Balazs et al. |
| 4,501,306 A | 2/1985 | Chu et al. |
| 4,582,640 A | 4/1986 | Smestad et al. |
| 4,582,865 A | 4/1986 | Balazs et al. |
| 4,605,691 A | 8/1986 | Balazs et al. |
| 4,636,524 A | 1/1987 | Balazs et al. |
| 4,642,117 A | 2/1987 | Nguyen et al. |
| 4,713,448 A | 12/1987 | Balazs et al. |
| 4,716,154 A | 12/1987 | Matson et al. |
| 4,772,419 A | 9/1988 | Matson et al. |
| 4,803,075 A | 2/1989 | Wallace et al. |
| 4,851,521 A | 7/1989 | della Valle et al. |
| 4,886,787 A | 12/1989 | De Belder et al. |
| 4,896,787 A | 1/1990 | Delamour et al. |
| 4,902,508 A | 2/1990 | Badylak et al. |
| 4,956,178 A | 9/1990 | Badylak et al. |
| 4,957,744 A | 9/1990 | della Valle et al. |
| 4,963,666 A | 10/1990 | Malson |
| 4,965,353 A | 10/1990 | della Valle et al. |
| 5,009,013 A | 4/1991 | Wiklund |
| 5,041,128 A | 8/1991 | Korthoff |
| 5,087,446 A | 2/1992 | Suzuki et al. |
| 5,091,171 A | 2/1992 | Yu et al. |
| 5,143,724 A | 9/1992 | Leshchiner et al. |
| 5,211,644 A | 5/1993 | VanBeek et al. |
| 5,246,698 A | 9/1993 | Leshchiner et al. |
| 5,281,422 A | 1/1994 | Badylak et al. |
| 5,314,874 A | 5/1994 | Miyata et al. |
| 5,328,955 A | 7/1994 | Rhee et al. |
| 5,336,767 A | 8/1994 | della Valle et al. |
| 5,352,463 A | 10/1994 | Badylak et al. |
| 5,356,883 A | 10/1994 | Kuo et al. |
| 5,372,821 A | 12/1994 | Badylak et al. |
| 5,399,351 A | 3/1995 | Leshchiner et al. |
| 5,403,345 A | 4/1995 | Spingler |
| 5,428,024 A | 6/1995 | Chu et al. |
| 5,445,833 A | 8/1995 | Badylak et al. |
| 5,516,533 A | 5/1996 | Badylak et al. |
| 5,520,916 A | 5/1996 | Dorigatti et al. |
| 5,527,856 A | 6/1996 | Rhee et al. |
| 5,531,716 A | 7/1996 | Luzio et al. |
| 5,550,187 A | 8/1996 | Rhee et al. |
| 5,565,519 A | 10/1996 | Rhee et al. |
| 5,571,503 A | 11/1996 | Mausner |
| 5,573,784 A | 11/1996 | Badylak et al. |
| 5,614,587 A | 3/1997 | Rhee et al. |
| 5,616,568 A | 4/1997 | Pouyani et al. |
| 5,616,611 A | 4/1997 | Yamamoto et al. |
| 5,616,689 A | 4/1997 | Shenoy et al. |
| 5,622,707 A | 4/1997 | Dorigatti et al. |
| 5,633,001 A | 5/1997 | Bengt Agerup |
| 5,641,518 A | 6/1997 | Badylak et al. |
| 5,643,464 A | 7/1997 | Rhee et al. |
| 5,644,049 A | 7/1997 | Giusti et al. |
| 5,645,860 A | 7/1997 | Knapp, Jr. et al. |
| 5,668,288 A | 9/1997 | Storey et al. |
| 5,676,964 A | 10/1997 | Della Valle et al. |
| 5,695,998 A | 12/1997 | Badylak et al. |
| 5,711,969 A | 1/1998 | Patel et al. |
| 5,718,012 A | 2/1998 | Cavallaro |
| 5,730,933 A | 3/1998 | Peterson |
| 5,733,868 A | 3/1998 | Peterson et al. |
| 5,735,863 A | 4/1998 | Della Valle et al. |
| 5,753,267 A | 5/1998 | Badyiak et al. |
| 5,755,791 A | 5/1998 | Whitson et al. |
| 5,762,966 A | 6/1998 | Knapp, Jr. et al. |
| 5,782,913 A | 7/1998 | Schindler et al. |
| 5,788,625 A | 8/1998 | Plouhar et al. |
| 5,823,671 A | 10/1998 | Mitchell et al. |
| 5,824,333 A | 10/1998 | Scopelianos et al. |
| 5,824,335 A | 10/1998 | Dorigatti et al. |
| 5,827,529 A | 10/1998 | Ono et al. |
| 5,827,937 A | 10/1998 | Agerup |
| 5,843,907 A | 12/1998 | Sakai et al. |
| 5,866,414 A | 2/1999 | Badylak et al. |
| 5,879,359 A | 3/1999 | Dorigatti et al. |
| 5,880,107 A | 3/1999 | Buenter |
| 5,885,619 A | 3/1999 | Patel et al. |
| 5,886,042 A | 3/1999 | Yu et al. |
| 5,922,028 A | 7/1999 | Plouhar et al. |
| 5,935,164 A | 8/1999 | Iverson |
| 5,941,910 A | 8/1999 | Schindler et al. |
| 5,972,326 A | 10/1999 | Galin et al. |
| 5,980,930 A | 11/1999 | Fenton et al. |
| 6,013,679 A | 1/2000 | Kuo et al. |
| 6,056,777 A | 5/2000 | McDowell |
| 6,066,325 A | 5/2000 | Wallace et al. |
| 6,086,578 A | 7/2000 | Adamyan et al. |
| 6,139,520 A | 10/2000 | McCrory et al. |
| 6,140,257 A | 10/2000 | Kershaw et al. |
| 6,224,857 B1 | 5/2001 | Romeo et al. |
| 6,312,421 B1 | 11/2001 | Boock |
| 6,335,035 B1 | 1/2002 | Drizen et al. |
| 6,339,074 B1 | 1/2002 | Cialdi et al. |
| 6,372,494 B1 | 4/2002 | Naughton et al. |
| 6,383,218 B1 | 5/2002 | Sourdille et al. |
| 6,383,219 B1 | 5/2002 | Telandro et al. |
| 6,387,413 B1 | 5/2002 | Miyata et al. |
| 6,418,934 B1 | 7/2002 | Chin |
| 6,432,710 B1 | 8/2002 | Boss, Jr. et al. |
| 6,521,223 B1 | 2/2003 | Calias et al. |
| 6,544,503 B1 | 4/2003 | Vanderhoff et al. |
| 6,579,978 B1 | 6/2003 | Renier et al. |
| 6,602,859 B2 | 8/2003 | Miyarnoto et al. |
| 6,627,620 B1 | 9/2003 | Nielsen |
| 6,630,486 B1 | 10/2003 | Royer |
| 6,632,802 B2 | 10/2003 | Bellini et al. |
| 6,638,538 B1 | 10/2003 | Hashimoto et al. |
| 6,685,963 B1 | 2/2004 | Taupin et al. |
| 6,716,251 B1 | 4/2004 | Asius et al. |

(56) References Cited

U.S. PATENT DOCUMENTS

| | | |
|---|---|---|
| 6,734,298 B1 | 5/2004 | Barbucci et al. |
| 6,767,924 B2 | 7/2004 | Yu et al. |
| 6,767,928 B1 | 7/2004 | Murphy et al. |
| 6,790,438 B1 | 9/2004 | Constancis et al. |
| 6,833,488 B2 | 12/2004 | Bucevschi et al. |
| 6,852,255 B2 | 2/2005 | Yang et al. |
| 6,872,819 B1 | 3/2005 | Pavesio et al. |
| 6,893,466 B2 | 5/2005 | Trieu |
| 6,903,199 B2 | 6/2005 | Moon et al. |
| 6,921,819 B2 | 7/2005 | Piron et al. |
| 6,924,273 B2 | 8/2005 | Pierce |
| 6,939,562 B2 | 9/2005 | Spiro et al. |
| 6,979,440 B2 | 12/2005 | Shefer et al. |
| 7,014,860 B1 | 3/2006 | Kawata et al. |
| 7,087,745 B1 | 8/2006 | Pallado et al. |
| 7,119,062 B1 | 10/2006 | Avis et al. |
| 7,125,860 B1 | 10/2006 | Renier et al. |
| 7,166,570 B2 | 1/2007 | Hunter et al. |
| 7,192,984 B2 | 3/2007 | Berg et al. |
| 7,196,180 B2 | 3/2007 | Aeschlimann et al. |
| 7,214,765 B2 | 5/2007 | Ringeisen et al. |
| 7,244,270 B2 | 7/2007 | Lesh |
| 7,314,636 B2 | 1/2008 | Caseres et al. |
| 7,323,425 B2 | 1/2008 | Chu et al. |
| 7,491,709 B2 | 2/2009 | Carey |
| 7,504,386 B2 | 3/2009 | Pressato et al. |
| 7,559,952 B2 | 7/2009 | Pinchuk |
| 7,637,900 B2 | 12/2009 | Burgess |
| 7,666,339 B2 | 2/2010 | Chaouk et al. |
| 7,741,476 B2 | 6/2010 | Lebreton |
| 7,807,656 B2 | 10/2010 | Reinmuller |
| 7,850,965 B2 | 12/2010 | Patel et al. |
| 7,902,171 B2 | 3/2011 | Reinmuller et al. |
| 7,910,690 B2 | 3/2011 | Ringeisen et al. |
| 7,998,202 B2 | 8/2011 | Lesh |
| 3,021,323 A1 | 9/2011 | Arora et al. |
| 3,033,665 A1 | 10/2011 | Burgess |
| 8,052,990 B2 | 11/2011 | Hermitte et al. |
| 8,124,120 B2 | 2/2012 | Sadozai et al. |
| 8,147,811 B1 | 4/2012 | Dalle Carbonare et al. |
| 8,240,314 B2 | 8/2012 | Fletcher |
| 8,318,695 B2 | 11/2012 | Stroumpoulis et al. |
| 8,338,375 B2 | 12/2012 | Schroeder et al. |
| 8,338,388 B2 | 12/2012 | Lebreton |
| 8,357,795 B2 | 1/2013 | Lebreton |
| 8,394,782 B2 | 3/2013 | Stroumpoulis et al. |
| 8,394,783 B2 | 3/2013 | Stroumpoulis et al. |
| 8,394,784 B2 | 3/2013 | Stroumpoulis et al. |
| 8,450,475 B2 | 5/2013 | Lebreton |
| 8,455,465 B2 | 6/2013 | Gavard Molliard |
| 8,513,216 B2 | 8/2013 | Stroumpoulis et al. |
| 8,524,213 B2 | 9/2013 | Leshchiner et al. |
| 8,563,532 B2 | 10/2013 | Lebreton et al. |
| 8,575,129 B2 | 11/2013 | Bellini et al. |
| 8,586,562 B2 | 11/2013 | Lebreton |
| 8,901,202 B2 | 12/2014 | Pastorello et al. |
| 9,228,027 B2 * | 1/2016 | Gurtner .................. A61L 15/28 |
| 2001/0008937 A1 | 7/2001 | Callegaro et al. |
| 2002/0026039 A1 | 2/2002 | Bellini et al. |
| 2002/0102311 A1 | 8/2002 | Gustavsson et al. |
| 2002/0160109 A1 | 10/2002 | Yeo et al. |
| 2003/0031638 A1 | 2/2003 | Joshi et al. |
| 2003/0068297 A1 | 4/2003 | Jain |
| 2003/0093157 A1 | 5/2003 | Casares et al. |
| 2003/0119985 A1 | 6/2003 | Sehl et al. |
| 2003/0148995 A1 | 8/2003 | Piron et al. |
| 2004/0006319 A1 | 1/2004 | Lina et al. |
| 2004/0032056 A1 | 2/2004 | Vang et al. |
| 2004/0101959 A1 | 5/2004 | Marko et al. |
| 2004/0127698 A1 | 7/2004 | Tsai et al. |
| 2004/0127699 A1 | 7/2004 | Zhao et al. |
| 2004/0192643 A1 | 9/2004 | Pressato et al. |
| 2004/0199241 A1 | 10/2004 | Gravett et al. |
| 2004/0265389 A1 | 12/2004 | Yul et al. |
| 2005/0033362 A1 | 2/2005 | Grafton |
| 2005/0101582 A1 | 5/2005 | Lyons et al. |
| 2005/0136122 A1 | 6/2005 | Sadozai et al. |
| 2005/0142152 A1 | 6/2005 | Leshchiner et al. |
| 2005/0181007 A1 | 8/2005 | Hunter et al. |
| 2005/0186261 A1 | 8/2005 | Avelar et al. |
| 2005/0186673 A1 | 8/2005 | Geistlich et al. |
| 2005/0187185 A1 | 8/2005 | Reinmuller |
| 2005/0226936 A1 | 10/2005 | Agerup et al. |
| 2005/0271729 A1 | 12/2005 | Wang |
| 2005/0281880 A1 | 12/2005 | Wang |
| 2005/0287180 A1 | 12/2005 | Chen |
| 2006/0040894 A1 | 2/2006 | Hunter et al. |
| 2006/0041320 A1 | 2/2006 | Matsuda |
| 2006/0073207 A1 | 4/2006 | Masters et al. |
| 2006/0095137 A1 | 5/2006 | Chung et al. |
| 2006/0105022 A1 | 5/2006 | Yokokawa et al. |
| 2006/0122147 A1 | 6/2006 | Wohlrab et al. |
| 2006/0136070 A1 | 6/2006 | Pinchuk |
| 2006/0141049 A1 | 6/2006 | Lyons et al. |
| 2006/0147483 A1 | 7/2006 | Chaouk et al. |
| 2006/0148755 A1 | 7/2006 | Bailleul |
| 2006/0166928 A1 | 7/2006 | Moon et al. |
| 2006/0189516 A1 | 8/2006 | Yang et al. |
| 2006/0194758 A1 | 8/2006 | Lebreton |
| 2006/0246137 A1 | 11/2006 | Hermitte et al. |
| 2006/0257488 A1 | 11/2006 | Hubbard |
| 2006/0264698 A1 | 11/2006 | Kondonis et al. |
| 2006/0286769 A1 | 12/2006 | Tsuchiya et al. |
| 2007/0026070 A1 | 2/2007 | Vonwiller et al. |
| 2007/0032805 A1 | 2/2007 | Therin et al. |
| 2007/0066816 A1 | 3/2007 | Tsai et al. |
| 2007/0077292 A1 | 4/2007 | Pinsky |
| 2007/0196426 A1 | 8/2007 | Hermitte et al. |
| 2007/0197754 A1 | 8/2007 | White et al. |
| 2007/0203095 A1 | 8/2007 | Sadozai et al. |
| 2007/0212385 A1 | 9/2007 | David |
| 2007/0224247 A1 | 9/2007 | Chudzik et al. |
| 2007/0224278 A1 | 9/2007 | Lyons et al. |
| 2007/0298005 A1 | 12/2007 | Thibault |
| 2008/0044476 A1 | 2/2008 | Lyons et al. |
| 2008/0057091 A1 | 3/2008 | Abdellaoui et al. |
| 2008/0089918 A1 | 4/2008 | Lebreton |
| 2008/0097605 A1 | 4/2008 | Pastorello et al. |
| 2008/0118563 A1 | 5/2008 | Muzzarelli et al. |
| 2008/0188416 A1 | 8/2008 | Bernstein |
| 2008/0193538 A1 | 8/2008 | Kitazono et al. |
| 2008/0200430 A1 | 8/2008 | Bitterrnan et al. |
| 2008/0207560 A1 | 8/2008 | Harada et al. |
| 2008/0207794 A1 | 8/2008 | Wright et al. |
| 2008/0241252 A1 | 10/2008 | Lyons et al. |
| 2008/0248079 A1 | 10/2008 | Dempsey et al. |
| 2008/0268051 A1 | 10/2008 | Hughes et al. |
| 2008/0274946 A1 | 11/2008 | Giampapa |
| 2008/0279806 A1 | 11/2008 | Cho |
| 2008/0293637 A1 | 11/2008 | Schroeder et al. |
| 2009/0017091 A1 | 1/2009 | Daniloff et al. |
| 2009/0018102 A1 | 1/2009 | Moutet et al. |
| 2009/0022808 A1 | 1/2009 | Champion et al. |
| 2009/0028817 A1 | 1/2009 | Niklason et al. |
| 2009/0030367 A1 | 1/2009 | Arora et al. |
| 2009/0036403 A1 | 2/2009 | Stroumpoulis et al. |
| 2009/0042834 A1 | 2/2009 | Karageozian et al. |
| 2009/0043268 A1 | 2/2009 | Eddy et al. |
| 2009/0093755 A1 | 4/2009 | Schroeder et al. |
| 2009/0110671 A1 | 4/2009 | Miyata et al. |
| 2009/0110736 A1 | 4/2009 | Boutros |
| 2009/0143331 A1 | 6/2009 | Stroumpoulis et al. |
| 2009/0143348 A1 | 6/2009 | Tezel et al. |
| 2009/0148527 A1 | 6/2009 | Robinson et al. |
| 2009/0155314 A1 | 6/2009 | Tezel et al. |
| 2009/0155362 A1 | 6/2009 | Longin et al. |
| 2009/0169615 A1 | 7/2009 | Pinsky |
| 2009/0204101 A1 | 8/2009 | Wortzman et al. |
| 2009/0209456 A1 | 8/2009 | Sweis |
| 2009/0263447 A1 | 10/2009 | Asius et al. |
| 2009/0291986 A1 | 11/2009 | Puppas et al. |
| 2009/0297632 A1 | 12/2009 | Waugh |
| 2010/0004198 A1 | 1/2010 | Stroumpoulis et al. |
| 2010/0028435 A1 | 2/2010 | Gavard Molliard |

(56) References Cited

U.S. PATENT DOCUMENTS

| | | |
|---|---|---|
| 2010/0028437 A1 | 2/2010 | Lebreton |
| 2010/0035838 A1 | 2/2010 | Heber et al. |
| 2010/0041788 A1 | 2/2010 | Voigts et al. |
| 2010/0098764 A1 | 4/2010 | Stroumpoulis et al. |
| 2010/0098794 A1 | 4/2010 | Armand |
| 2010/0099623 A1 | 4/2010 | Schroeder et al. |
| 2010/0111919 A1 | 5/2010 | Abuzaina et al. |
| 2010/0136070 A1 | 6/2010 | Dobak et al. |
| 2010/0221684 A1 | 9/2010 | Asius et al. |
| 2010/0226988 A1 | 9/2010 | Lebreton |
| 2010/0255068 A1 | 10/2010 | Stroumpoulis et al. |
| 2010/0303873 A1 | 12/2010 | Piron et al. |
| 2010/0310631 A1 | 12/2010 | Domard et al. |
| 2010/0316683 A1 | 12/2010 | Piron et al. |
| 2011/0034684 A1 | 2/2011 | Yokokawa et al. |
| 2011/0077737 A1 | 3/2011 | Stroumpoulis et al. |
| 2011/0113206 A1 | 5/2011 | Lebreton |
| 2011/0171286 A1 | 7/2011 | Cecile et al. |
| 2011/0171311 A1 | 7/2011 | Gousse et al. |
| 2011/0172180 A1 | 7/2011 | Gousse et al. |
| 2011/0224164 A1 | 9/2011 | Lebreton |
| 2011/0229574 A1 | 9/2011 | Guillen et al. |
| 2011/0263724 A1 | 10/2011 | Gurtner et al. |
| 2012/0010146 A1 | 1/2012 | Han et al. |
| 2012/0013959 A1 | 1/2012 | Andersson et al. |
| 2012/0034462 A1 | 2/2012 | Stroumpoulis et al. |
| 2012/0071437 A1 | 3/2012 | Stroumpoullis et al. |
| 2012/0095206 A1 | 4/2012 | Chen et al. |
| 2012/0100217 A1 | 4/2012 | Green et al. |
| 2012/0164098 A1 | 6/2012 | Schroeder et al. |
| 2012/0172328 A1 | 7/2012 | Lebreton |
| 2012/0189589 A1 | 7/2012 | Van Epps et al. |
| 2012/0189590 A1 | 7/2012 | Van Epps et al. |
| 2012/0189708 A1 | 7/2012 | Van Epps et al. |
| 2012/0190644 A1 | 7/2012 | D'este et al. |
| 2012/0208890 A1 | 8/2012 | Gousse et al. |
| 2012/0225842 A1 | 9/2012 | Cecile et al. |
| 2012/0232030 A1 | 9/2012 | Gousse et al. |
| 2013/0013415 A1 | 1/2013 | Brown et al. |
| 2013/0023653 A1 | 1/2013 | Stroumpoulis et al. |
| 2013/0041038 A1 | 2/2013 | Lebreton |
| 2013/0041039 A1 | 2/2013 | Lebreton |
| 2013/0072453 A1 | 3/2013 | Gousse et al. |
| 2013/0096081 A1 | 4/2013 | Njikang et al. |
| 2013/0116188 A1 | 5/2013 | Pollock et al. |
| 2013/0116190 A1 | 5/2013 | Pollock et al. |
| 2013/0116411 A1 | 5/2013 | Pollock et al. |
| 2013/0122063 A1 | 5/2013 | Fermanian et al. |
| 2013/0123210 A1 | 5/2013 | Liu et al. |
| 2013/0131011 A1 | 5/2013 | Lebreton |
| 2013/0136780 A1 | 5/2013 | Tezel et al. |
| 2013/0142731 A1 | 6/2013 | Gurtner et al. |
| 2013/0203696 A1 | 8/2013 | Njikang et al. |
| 2013/0209532 A1 | 8/2013 | Stroumpoulis et al. |
| 2013/0210760 A1 | 8/2013 | Liu et al. |
| 2013/0226235 A1 | 8/2013 | Fermanian et al. |
| 2013/0237615 A1 | 9/2013 | Meunier et al. |
| 2013/0244943 A1 | 9/2013 | Yu et al. |
| 2013/0244970 A1 | 9/2013 | Lebreton |
| 2013/0274222 A1 | 10/2013 | Horne et al. |
| 2014/0011980 A1 | 1/2014 | Chitre et al. |
| 2014/0011990 A1 | 1/2014 | Lebreton |
| 2014/0228971 A1 | 8/2014 | Kim |

FOREIGN PATENT DOCUMENTS

| | | |
|---|---|---|
| DE | 2912043 A1 | 1/1980 |
| EP | 0273823 A1 | 7/1988 |
| EP | 0193510 B1 | 11/1988 |
| EP | 0341745 A1 | 11/1989 |
| EP | 0416250 A2 | 3/1991 |
| EP | 0416846 A2 | 3/1991 |
| EP | 1217008 A1 | 6/2002 |
| EP | 1247522 A1 | 10/2002 |
| EP | 1398131 A1 | 3/2004 |
| EP | 1419792 A1 | 5/2004 |
| EP | 1532991 A1 | 5/2005 |
| EP | 1614696 A1 | 1/2006 |
| EP | 1640026 A1 | 3/2006 |
| EP | 1712228 A2 | 10/2006 |
| EP | 1726299 A2 | 11/2006 |
| EP | 2236523 A1 | 6/2010 |
| FR | 2733427 A1 | 10/1996 |
| FR | 2920000 B1 | 2/2009 |
| FR | 2924615 B1 | 6/2009 |
| JP | 550153711 | 11/1980 |
| JP | 11-511344 | 10/1999 |
| JP | 2000-210376 A | 8/2000 |
| JP | 2000-271207 A | 10/2000 |
| JP | 2000-516978 A | 12/2000 |
| JP | 2002-080501 | 3/2002 |
| JP | 2003-521962 A | 7/2003 |
| JP | 2006-504930 A | 2/2006 |
| JP | 2006-522851 A | 10/2006 |
| JP | 2007-502430 A | 2/2007 |
| JP | 2007-063177 | 3/2007 |
| JP | 2007-516333 A | 6/2007 |
| JP | 2007-520612 A | 7/2007 |
| JP | 2007-262595 A | 10/2007 |
| JP | 2009-503281 A | 1/2009 |
| KR | 20080062092 A | 7/2008 |
| WO | 1986000079 A1 | 1/1986 |
| WO | 1986000912 A1 | 2/1986 |
| WO | 1992000105 A1 | 1/1992 |
| WO | 199213579 A1 | 8/1992 |
| WO | 1992020349 A1 | 11/1992 |
| WO | 1996033751 A1 | 10/1993 |
| WO | 1994001468 A1 | 1/1994 |
| WO | 1994002517 A1 | 3/1994 |
| WO | 199524497 A2 | 9/1995 |
| WO | 199637519 A1 | 11/1996 |
| WO | 1997004012 A1 | 2/1997 |
| WO | 199737613 A1 | 10/1997 |
| WO | 199803876 A1 | 3/1998 |
| WO | 1998035639 A1 | 8/1998 |
| WO | 1998035640 A1 | 8/1998 |
| WO | 199904828 A2 | 2/1999 |
| WO | 199956799 A1 | 11/1999 |
| WO | 2000001428 A1 | 1/2000 |
| WO | 200100190 A2 | 1/2001 |
| WO | 2001079342 A2 | 10/2001 |
| WO | 2002005753 A1 | 1/2002 |
| WO | 2002006350 A1 | 1/2002 |
| WO | 2002009792 A1 | 2/2002 |
| WO | 200217979 A2 | 3/2002 |
| WO | 2003007782 A2 | 1/2003 |
| WO | 2002017713 A1 | 3/2003 |
| WO | 2004020473 A1 | 3/2004 |
| WO | 2004022603 A1 | 3/2004 |
| WO | 2004073759 A1 | 9/2004 |
| WO | 2004092222 A2 | 10/2004 |
| WO | 2004092223 A1 | 10/2004 |
| WO | 2005012364 A2 | 2/2005 |
| WO | 2005040224 A1 | 6/2005 |
| WO | 2005067994 A1 | 7/2005 |
| WO | 2005074913 A2 | 8/2005 |
| WO | 2005085329 A1 | 9/2005 |
| WO | 2005097218 A2 | 10/2005 |
| WO | 2005112888 A2 | 12/2005 |
| WO | 2006023645 A2 | 3/2006 |
| WO | 2006067608 A1 | 6/2006 |
| WO | 2007018124 A1 | 2/2007 |
| WO | 2007070617 A1 | 6/2007 |
| WO | 2007077399 A3 | 7/2007 |
| WO | 2007128923 A3 | 11/2007 |
| WO | 2007136738 A2 | 11/2007 |
| WO | 2008034176 A1 | 3/2008 |
| WO | 2008056069 A1 | 5/2008 |
| WO | 2008068297 A1 | 6/2008 |
| WO | 2008072230 A1 | 6/2008 |
| WO | 2008077172 A2 | 7/2008 |
| WO | 2008098019 A2 | 8/2008 |
| WO | 2008139122 A2 | 11/2008 |
| WO | 2008147817 A2 | 12/2008 |

(56) References Cited

FOREIGN PATENT DOCUMENTS

| | | | |
|---|---|---|---|
| WO | 2008148967 A2 | 12/2008 | |
| WO | 2008157280 A1 | 12/2008 | |
| WO | 2008157608 A1 | 12/2008 | |
| WO | 2009024719 A1 | 2/2009 | |
| WO | 2009026158 A3 | 2/2009 | |
| WO | 2009028764 A1 | 3/2009 | |
| WO | 2009034559 A2 | 3/2009 | |
| WO | 2009073437 A1 | 6/2009 | |
| WO | 2010003797 A1 | 1/2010 | |
| WO | 2010015900 A1 | 2/2010 | |
| WO | 2010027471 A2 | 3/2010 | |
| WO | 2010028025 A1 | 3/2010 | |
| WO | 2010029344 A3 | 3/2010 | |
| WO | 2010038771 A1 | 4/2010 | |
| WO | 2010051641 A1 | 5/2010 | |
| WO | 2010052430 A2 | 5/2010 | |
| WO | 2010053918 A1 | 5/2010 | |
| WO | 2010061005 A1 | 6/2010 | |
| WO | 2011109129 A1 | 9/2011 | |
| WO | 2011109130 A1 | 9/2011 | |
| WO | 2012054301 A1 | 4/2012 | |
| WO | 2012054311 A1 | 4/2012 | |
| WO | 2012077055 A1 | 6/2012 | |
| WO | 2012089179 A1 | 7/2012 | |
| WO | 2013055832 A1 | 4/2013 | |
| WO | 2012174464 A3 | 5/2014 | |

OTHER PUBLICATIONS

Aesthetic Buyers Guide, Juvederm Raises Standards, 2007, 1, 4-7; miinews.com.
Albano, Emanuele et al., Hydroxyethyl Radicals in Ethanol Hepatotoxicity, Frontiers in Bioscience, 1999, 533-540, 4.
Allemann, Inja Bogdan, Hyaluronic Acid Gel (Juvederm) Preparations in the Treatment of Facial Wrinkles and Folds, Clinical Interventions in Aging, 2008, 629-634, 3 (4).
Andre, Pierre MD, Hyaluronic Acid and Its Use as a "Rejuvenation" Agent in Cosmetic Dermatology, Seminars in Cutaneous Medicine and Surgery, 2004, 218-222, Elsevier, Inc.
Antunes, Alberto et al., Efficacy of Intrarectal Lidocaine Hydrochloride Gel for Pain Control in Patients Undergoing Transrectal Prostate Biopsy, Clinical Urology, 2004, 380-383, 30.
Atanassoff, Peter et al., The Effect of Intradermal Administration of Lidocaine and Morphine on the Response to Thermal Stimulation, Anesth Analg, 1997, 1340-1343, 84.
Baumann, Leslie et al., Comparison of Smooth-Gel Hyaluronic Acid Dermal Fillers with Cross-linked Bovine Collagen: A Multicenter, Double-Masked, Randomized, Within-Subject Study, Dermatologic Surgery, 2007, S128-135, 33 (2).
Beasley, Karen et al., Hyaluronic Acid Fillers: A Comprehensive Review, Facial Plast. Surg., 2009, 86-94, 25(2).
Beer, Kenneth, Dermal Fillers and Combinations of Fillers for Facial Rejuvenation, Dermatologic Clin, 2009, 427-432, 27 (4).
Belda, Jose et al., Hyaluronic Acid Combined With Mannitol to Improve Protection Against Free-Radical Endothelial Damage: Experimental Model, J Cataract Refract Surg, 2005, 1213-1218, 31.
Bircher, Andres et al., Delayed-type Hypersensitivity to Subcutaneous Lidocaine With Tolerance to Articaine: Confirmation by In Vivo and In Vitro Tests, Contact Dermatitis, 1996, 387-389, 34.
Bleyer, Mark, SIS Facial Implant 510(k) Summary, Cook Biotech Inc., May 19, 2005.
Bluel, K. et al., Evaluation of Reconstituted Collagen Tape as a Model for Chemically Modified Soft Tissues, Biomat., Med. Dev., Art. Org., 1981, 37-46, 9(1).
Boulle et al., Lip Augmentation and Contour Correction With a Ribose Cross-linked Collagen Dermal Filler, Journal of Drugs in Dermatology, Mar. 2009, 1-8, vol. 8 Issue 3.
Buck, Donald, Injectable Fillers for Facial Rejuvenation: A Review, Journal of Plastic, Reconstructive & Aesthetic Surgery, 2009, 11-18, 62.
Capozzi, Angelo et al., Distant Migration of Silicone Gel From a Ruptured Breast Implant, Silicone Gel Migration, 1978, 302-3, 62 (2).
Carlin, G. et al., Effect of Anti-Inflammatory Drugs on Xanthine Oxidase and Xanthine Oxidase Induced Depolyrnerization of Hyaluronic Acid, Agents and Actions, 1985, 377-384 16 (5).
Carruthers et al., The Science and Art of Dermal Fillers for Soft-Tissue Augmentation, Journal of Drugs in Dermatology, Apr. 2009, 335-350, vol. 8 Issue 4.
Champion, Julie et al., Role of Target Geometry in Phagocytosis, Proc. Nat. Acad. Sci., 2006, 4930-4934, 103 (13).
Chin, Thomas et al., Allergic Hypersensitivity to Lidocaine Hydrochloride, International Society of Tropical Dermatology, 1980, 147-148.
Chvapil, Milos, Collagen Sponge: Theory and Practice of Medical Applications, J. Biomed. Mater. Res., 1977, 721-741, 11.
Clark, D. Dick et al., The Influence of Triamcinolone Acetonide on Joint Stiffness in the Rat, The Journal of Bone and Joint Surgery, 1971, 1409-1414, 53A (7).
Cohen, Miriam et al., Organization and Adhesive Properties of the Hyaluronan Pericellular Coat of Chondrocytes and Epithelial Cells, Biophysical Journal, 2003, 1996-2005, 85.
Conley et al., Thread Augmentation for Facial Rhytides, Annals of Plastic Surgery, Aug. 1979, 118-126.
Cui, Yu et al., The Comparison of Physicochemical Properties of Four Cross-linked Sodium Hyaluronate Gels With Different Cross-linking Agents, Advanced Materials Research, 2012, 1506-1512, 396-398.
Deland, Frank, Intrathecal Toxicity Studies with Benzyl Alcohol, Toxicology and Applied Pharmacology, 1973, 153-6, 25, Academic Press, Inc.
Desai, Ur et al., Molecular Weight of Heparin Using 13C Nuclear Magnetic Resonance Spectroscopy, J Pharm Sci., 1995, 212-5, 84 (2).
Elvassore et al., Production of Different Morphologies of Biocompatible Polymeric Materials by Supercritical CO2 Antisolvent Techniques, Biotechnology and Bioengineering, 2001, 449-457.
Eyre, David R. et al., Collagen Cross-Links, Topics in Current Chemistry, 2005, 207-229, 247, US.
Falcone et al., Temporary Polysaccharide Dermal Fillers: A Model for Persistence Based on Physical Properties, Dermatologic Surgery, Aug. 2009, 1238-1243, 35; 8.
Falcone, Samuel et al., Crosslinked Hyaluronic Acid Dermal Fillers: A Comparison of Rheological Properties, Journal of Biomedical Materials Research, 2008, 264-271, 87 (1).
Farley, Jon et al., Diluting Lidocaine and Mepivacaine in Balanced Salt Solution Reduces the Pain of Intradermal Injection, Regional Anesthesia, 1994, 48-51, 19 (1).
Frati, Elena et al., Degradation of Hyaluronic Acid by Photosensitized Riboflavin In Vitro. Modulation of the Effect by Transition Metals, Radical Quenchers, and Metal Chelators, Free Radical Biology Medicine, 1996, 1139-1144, 22 (7).
Fujinaga, Masahiko et al., Reproductive and Teratogenic Effects of Lidocaine in Sprague-Dawley Rats, Anesthesiology, 1986, 626-632, 65.
Gammaitoni, Arnold et al., Pharmacokinetics and Safety of Continuously Applied Lidocaine Patches 5%, Am J Health Syst Pharm, 2002, 2215-2220, 59.
Ginshicel MH, Hydroxy Propyl Methyl Cellulose, Retrieved on Nov. 12, 2008 http://www.ginshicel.cn/MHPC.html, 2007, p. 1-3, 2 (3).
Gold, Michael, Use of Hyaluronic Acid Fillers for the Treatment of the Aging Face, Clin. Interventions Aging, 2007, 369-376, 2 (3).
Goldberg, David, Breakthroughs in US dermal fillers for facial soft-tissue augmentation, Journal of Cosmetic and Laser Therapy, 2009, 240-247, 11, Informa UK Ltd.
Graefe, Hendrik et al., Sensitive and Specific Photometric Determination of Mannitol, Clin Chem Lab Med, 2003, 1049-1055, 41 (8).
Grecomoro, G. et al., Intra-articular treatment with sodium hyaluronate in gonarthrosis: a controlled clinical trial versus placebo, Pharmatherapeutica, 1987, 137-141, 5 (2).

(56) References Cited

OTHER PUBLICATIONS

Grillo, Hermes et al., Thermal Reconstitution of Collagen From Solution and the Response to Its Heterologous Implantation, JSR, 1962, 69-82, 2 (1).

Haaf et al., Resorbable suture material in the human skin: tissue reaction and modified suture technic, Hautarzt, Jan. 1988, 39(1), (Abstract only).

Hassan, HG et al., Effects of Adjuvants to Local Anaesthetics on Their Duration. III. Experimental Studies of Hyaluronic Acid, Acta Anaesthesiol Scand., 1985, 1, 29 (4).

Hayashibara, AA2G, Sep. 23, 2007, Retrieved on Jan. 17, 2012, http://web.archive.org/web/20070923072010/http://www.hayashibara-intl.cosmetics/aa2g.html.

Helary, Christophe et al., Concentrated Collagen Hydrogels as Dermal Substitutes, Biomaterials, 2010, 481-490, 31.

Helliwell, Philip, Use of an objective measure of articular stiffness to record changes in finger joints after intra-articular injection of corticosteroid, Annals of Rheumatic Diseases, 1997, 71-73, 56.

Hertzberger-Ten, Cate et al., Intra-articular steroids in pauciarticular juvenile chronic arthritis, type 1, European Journal of Pediatrics, 1991, 170-172, 150.

Hetherington, NJ et al., Potential for Patient Harm from Intrathecal Administration of Preserved Solutions, Med J Aust., 2000, 1, 173(3).

Holzheimer, R.G., Adverse Events of Sutures: Possible Interactions of Biomaterials?, European Journal of Medical Research, 2006, 521-526, 10, I. Holzapfel Publishers.

Hurst, E., Adhesive Arachnoiditis and Vascular Blockage Caused by Detergents and Other Chemical Irritants: An Experimental Study, J Path. Bact., 1955, 167, 70.

Intramed (PTY) Ltd, Intramed Mannitol 20% m/v Infusion, Package Insert, Jan. 1979, 4 pages, 12-214/8-94, ZA.

Jones, Adrian C. et al., Intra-articular hyaluronic acid compared to intra-articular triamcinolone hexacetonide in inflammatory knee osteoarthritis, Osteoarthritis and Cartilage, 1995, 269-273, 3.

Kablik, Jeffrey et al., Comparative Physical Properties of Hyaluronic Acid Dermal Fillers, Dermatol Surg, 2009, 302-312, 35.

Klein, Arnold William, Skin Filling Collagen and Other Injectables of the Skin, Dermatologic Clinics, Jul. 2001, 491-508, 19 (3), US.

Kopp, et al., The Short-term Effect of Intra-articular Injections of Sodium Hyaluronate and Corticosteroid on Temporomandibular Joint Pain and Dysfunction, Journal of Oral and Maxillofacial Surgery, 1985, 429-435, 43.

Kulicke, Werner-Michael et al., Visco-Elastic Properties of Sodium Hyaluronate Solutions, Institute for Technical and Macromolecular Chemistry, 2008, 585-587, DE.

Laeschke, Klaus, Biocompatibility of Microparticies Into Soft Tissue Fillers, Semin Cutan Med Surg, 2004, 214-217, 23.

Lamar, PD et al., Antifibrosis Effect of Novel Gels in Anterior Ciliary Sclerotomy (ACS), 2002, 1 Page, The Association for Research in Vision and Ophthalrnology, Inc.

Lapcik et al., Hyaluronan: Preparation, Structure, Properties, and Applications, Chemical Reviews, Dec. 1998. 2663-2684. vol. 98. No. 8.

Leach et al., Hyaluronan, Encyclopedia of Biomaterials and Biomedical Engineering, 2004, 779-789.

Levy, Jaime et al., Lidocaine Hypersensitivity After Subconjunctival Injection, Can J Ophthalmol, 2006, 204-206, 41.

Lindvall, Sven et al., Influence of Various Compounds on the Degradation of Hyaluronic Acid by a Myeloperoxidase System, Chemico-Biological Interactions, 1994, 1-12, 90.

Lupo, Mary, Hyaluronic Acid Fillers in Facial Rejuvenation, Seminars in Cutaneous Medicine and Surgery, 2006, 122-126, 25.

Mackley, Christine et al., Delayed-Type Hypersensitivity to Lidocaine, Arch Dermatol, 2003, 343-346, 139.

Mancinelli, Laviero et al., Intramuscular High-dose Triamcinolone Acetonide in the Treatment of Severe Chronic Asthma, West J Med, 1997, 322-329, 167 (5).

Matsumoto, Alan et al., Reducing the Discomfort of Lidocaine Administration Through pH Buffering, Journal of Vascular and Interventional Radiology, 1994, 171-175, 5 (1).

McCarty, Dj, et al., Inflammatory Reaction After Intrasynovial Injection of Microcrystalline Andrenocorticosteroid Esters, Arthritis and Rheumatism, Aug. 1964, 359-367, vol. VII, No. 4, Grune & Stratton.

McCleland, Marcee et al., Evaluation of Artecoll Polymethylmethacrylate Implant for Soft-Tissue Augmentation: Biocompatibility and Chemical Characterization, Plastic & Reconstructive Surgery, 1997, 1466-1474, 100 (6).

McPherson, John et al., Development and Biochemical Characterization of Injectable Collagen, Journal of Dermatol Surg Oncol, 1988, 13-20, 14 (Suppl) 1) 7.

Millay, Donna et al., Vasoconstrictors in Facial Plastic Surgery, Arch Otolaryngol Head Neck Surg., 1991, 160-163, 117.

Niamtu III, DMD, Joseph, Advanta Facial Implants, Oral Maxillofacial Surg Clin N Am, 2005, 29-39, 17.

Orvisky, E. et al., High-molecular-weight Hyaluronan—a Valuable Tool in Testing the Antioxidative Activity of Amphiphilic Drugs Stobadine and Vinpocetine, Journal of Pharm. Biomed. Anal., 1997, 419-424 16.

Osmitrol (generic name Mannitol), Official FDA Information, side effects and uses, http://www.drugs.com/pro/osmitrol.html, 2010, 10 Pages.

Osol, Arthur, Remington's Pharmaceutical Sciences, Mack Publishing Company, 1980, 10 pgs, 16th Edition, Easton, Pennsylvania, US.

Park, DJ et al., In Vitro Evaluation of Conjugated Hyaluronic Acid With Ascorbic Acid, Journal of Bone and Joint Surgery, 2010, 115, 92.

Park, Si-Nae et al., Biological Characterization of EDC-Crosslinked Collagen-Hyaluronic Acid Matrix in Dermal Tissue Restoration, Biomaterials, 2003, 1631-1641, 24.

Park, Si-Nae et al., Characterization of Porous Collagen/Hyaluronic Acid Scaffold Modified by 1-Ethyl-3-(3-Dimethylaminopropyl)Carbodiimide Cross-Linking, Biomaterials, 2002, 1205-1212, 23.

Powell, Michael, Stability of Lidocaine in Aqueous Solution: Effect of Temperature, pH, Buffer, and Metal Ions on Amide Hydrolysis, Pharmaceutical Research, 1987, 42-45, 4 (1).

Prestwich, Glenn, Evaluating Drug Efficacy and Toxicology in Three Dimensions: Using Synthetic Extracellular Matrices in Drug Discovery, Accounts of Chemical Research, Jan. 2008, 139-148, 41(1).

Rehakova, Milena et al., Properties of Collagen and Hyaluronic Acid Composite Materials and Their Modification by Chemical Crosslinking, Journal of Biomedical Materials Research, 1996, 369-372, 30, US.

Rinaudo, Marguerite, Main properties and current applications of some polysaccharides as biomaterials, Polymer international. 2008, 397-430, 57.

Rosenblatt, J. et al., Chain Rigidity and Diffusional Release in Biopolymer Gels, Controlled Release Society, 1993, 264-265, 20.

Rosenblatt, J. et al., The Effect of Collagen Fiber Size Distribution on the Release Rate of Proteins From Collagen Matrices by Diffusion, J Controlled Release, 1989, 195-203, 9.

Sannino, A. et al., Crosslinking of Cellulose Derivatives and Hyaluronic Acid With Water-Soluble Carbodiimide, Polymer, 2005, 11206-11212, 46.

Sculptra Product Information, Dermik Laboratories, Jun. 1-10, 2004.

Segura, Tatiana et al., Crosslinked Hyaluronic Add Hydrogels: A Strategy to Functionalize and Pattern, Biomaterials, 2005, 359-371, 26 (4).

Selvi, Enrico et al., Arthritis Induced by Corticosteroid Crystals, The Journal of Rheumatology, 2004, 622, 31 (3).

Semchyshyn, N.L., Dermatologic Surgical Complications, Drugs, Diseases and Procedures, 2012, 1-20.

Serban, Monica et al., Modular Extracellular Matrices: Solutions for the Puzzle, Methods, 2008, 93-98, 45 (1).

(56) References Cited

OTHER PUBLICATIONS

Shu, Xiao et al, Synthesis and evaluation of injectable, in situ crosslinkable synthetic extracellular matrices for tissue engineering, Journal of Biomedical Materials Research, 2006, 902-912, 79A.

Silver, Frederick et al., Physical Properties of Hyaluronic Acid and Hydroxypropylmethylcellulose in Solution: Evaluation of Coating Ability, Journal of Applied Biomaterials, 1994, 89-98, 5.

Skardal, Aleksander et al., Bioprinting Vessel-Like Constructs Using Hyaluronan Hydrogels Crosslinked With Tetrahedral Polyethylene Glycol Tetracrylates, Biomaterials, 2010, 6173-6181, 31.

Smith, Kevin et al., Five Percent Lidocaine Cream Applied Simultaneously to the Skin and Mucosa of the Lips Creates Excellent Anesthesia for Filler Injections, Dermatol Surg, 2005, 1635-1637, 31.

Tezel et al., The science of hyaluronic acid dermal fillers, Journal of Cosmetic and Laser Therapy, 2008, 35-42, 10.

Thermo Scientific Pierce Crosslinking Technical Handbook, Apr. 2009, 1-48.

Truswell, MD, William H., Dual-Porosity Expanded Polytetrafluoroethylene Soft Tissue Implant, Arch Facial Plast Surg, Apr. 2002, 92-97, 4(2).

Visiol, Viscoelstic Gel for Use in Ocular Surgery, http://www.trbchemedica.com/index.php/option=com_content&tas, 2010, 1 Page.

Wahl, Gregor, European Evaluation of a New Hyaluronic Acid Filler Incorporating Lidocaine, Journal of Cosmetic Dermatology, 2008, 298-303, 7.

Wang, Frank et al., In Vivo Stimulation of De Novo Collagen Production Caused by Cross-Linked Hyaluronic Acid Dermal Filler Injections in Photodamaged Human Skin, Arch Dermatol, Feb. 2007, 155-163, 143.

Waraszkiewicz, Sigmund et al., Stability-Indicating High-Performance Liquid Chromatographic Analysis of Lidocaine Hydrochloride and Lidocaine Hydrochloride with Epinephrine Injectable Solutions, J of Pharmaceutical Sciences, 1981, 1215-1218, 70 (11).

Weidmann, Michael, New Hyaluronic Acid Filler for Subdermal and Long-lasting Volume Restoration of the Face, European Dermatology, 2009, 65-68.

Xia, Yun et al., Comparison of Effects of Lidocaine Hydrochloride, Buffered Lidocaine, Diphenhydramine, and Normal Saline After Intradermal Injection, J of Clinical Anesthesia, 2002, 339-343, 14.

Yeom, Junseok et al., Effect of Cross-linking Reagents for Hyaluronic Acid Hydrogel Dermal Fillers on Tissue Augmentation and Regeneration, Bioconjugate Chemistry, 2010, 240, 21, American Chemical Society.

Yui, Nobuhiko et al., Inflammation Responsive Degradation of Crosslinked Hyaluronic Acid Gels, Journal of Controlled Release, 1992, 105-116, 26.

Yui, Nobuhiko et al., Photo-Responsive Degradation of Heterogeneous Hydrogels Comprising Crosslinked Hyaluronic Acid and Lipid Microspheres for Temporal Drug Delivery, Journal of Controlled Release, 1993, 141-145, 26.

Yun, Yang H. et al., Hyaluronan Microspheres for Sustained Gene Delivery and Site-Specific Targeting, Biomaterials, 2004, 147-157, 25, US.

Zheng et al., In Situ Crosslinkable Hyaluronan Hydrogels for Tissue Engineering, Biomaterials, 2004, 1339-1348, 25.

Zulian, F. et al., Triamcinolone Acetonide and Hexacetonide Intra-Articular Treatment of Symmetrical Joints in Juvenile Idiopathic Arthritis: A Double-Blind Trial, Rheumatology, 2004, 1288-1291, 43.

* cited by examiner

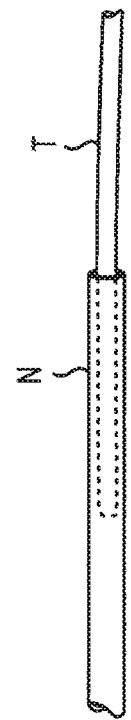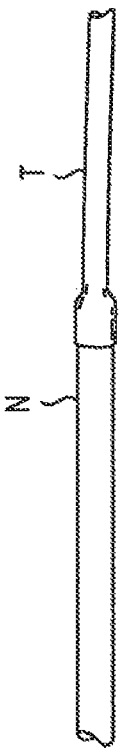

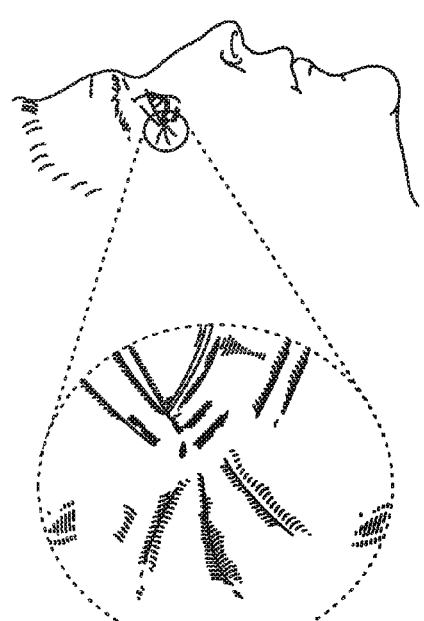
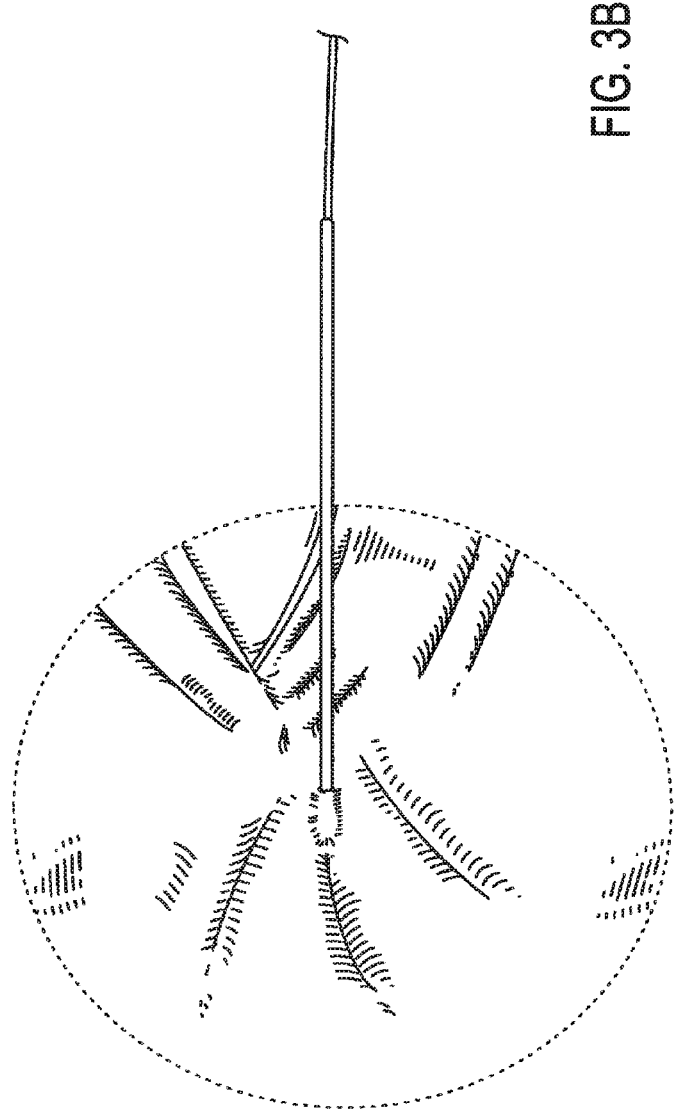
FIG. 3A
FIG. 3B

THREADS OF HYALURONIC ACID AND/OR DERIVATIVES THEREOF, METHODS OF MAKING THEREOF AND USES THEREOF

CROSS REFERENCE TO RELATED APPLICATIONS

This application is a continuation of United States National Stage application Ser. No. 13/060,919, filed May 19, 2011 which is a 371 of PCT/US09/55704, filed Sep. 2, 2009, which claims benefit under 35 U.S.C. §119(e) from U.S. Provisional Application Ser. No. 61/190,866, filed Sep. 2, 2008.

FIELD

The present invention relates generally to threads of hyaluronic acid, and/or derivatives thereof, methods of making thereof and uses thereof, for example, in aesthetic applications (e.g., dermal fillers), surgery (e.g., sutures), drug delivery, negative pressure wound therapy, moist wound dressing, etc.

BACKGROUND

Hyaluronic acid is a linear polysaccharide (i.e., non-sulfated glycosaminoglycan) consisting of a repeated disaccharide unit of alternately bonded β-D-N-acetylglucosamine and β-D-glucuronic acid (i.e., $(-4GlcUA\beta 1-3GlcNAc\beta 1-)_n$) which is a chief component of the extracellular matrix and is found, for example, in connective, epithelial and neural tissue. Natural hyaluronic acid is highly biocompatible because of its lack of species and organ specificity and thus is often used as a biomaterial in tissue engineering and as a common ingredient in various dermal fillers.

Various chemically modified forms of hyaluronic acid (e.g., cross linked forms, ionically modified forms, esterified forms, etc.) have been synthesized to address a significant problem associated with natural hyaluronic acid which has poor in vivo stability due to rapid enzymatic degradation and hydrolysis. Currently, hyaluronic acid or cross linked versions thereof are used in various gel forms, for example as dermal fillers, adhesion barriers, etc.

However, substantial issues exist with the use of gels of hyaluronic acid or cross linked versions thereof. First, the force required to dispense gels of hyaluronic acid or cross linked versions thereof is non-linear which causes the initial "glob" that many physicians report when injecting hyaluronic acid or cross linked versions thereof. Second, precisely dispensing hyaluronic gels to specific locations is very difficult because such gels have little mechanical strength. Further, the gel will occupy the space of least resistance which makes its use in many applications (e.g., treatment of fine wrinkles) problematic.

Accordingly, what is needed are new physical forms of hyaluronic acid or cross linked versions thereof which can be dispensed uniformly to specific locations regardless of tissue resistance. Such new forms may have particular uses, for example, in aesthetic and surgical applications, drug delivery, wound therapy and wound dressing.

SUMMARY

The present invention satisfies these and other needs by providing, in one aspect, a thread of hyaluronic acid or salts, hydrates or solvates thereof and, in a second aspect, a thread of cross linked hyaluronic acid or salts, hydrates or solvates thereof. In some embodiments, the thread is a combination of a thread of hyaluronic acid or salts, hydrates or solvates thereof and a thread of cross linked hyaluronic acid or salts, hydrates or solvates thereof.

In a third aspect, a method of making a thread of hyaluronic acid or salts, hydrates or solvates thereof is provided. Hyaluronic acid or salts, hydrates or solvates thereof are mixed with water or a buffer to form a gel. The gel is extruded to form a thread. The thread is then dried to provide a thread of hyaluronic acid.

In a fourth aspect, a method of making a thread of cross linked hyaluronic acid or salts, hydrates or solvates thereof is provided. Hyaluronic acid or salts, hydrates or solvates thereof are mixed with water or a buffer and a cross linking agent to form a gel. The gel is extruded to form a thread. The thread is then dried to provide a thread of cross linked hyaluronic acid.

In a fifth aspect a method of treating a wrinkle in a subject in need thereof is provided. A thread of hyaluronic acid or salts, hydrates or solvates thereof or a thread of cross linked hyaluronic acid or salts, hydrates or solvates thereof or a combination thereof is attached to the proximal aspect of a needle. The distal end of the needle is inserted through the skin surface of the subject into the dermis adjacent to or within the wrinkle. The dermis of the subject in the base of the wrinkle is traversed with the needle. The needle then exits the skin surface of the subject and is pulled distally until it is removed from the skin of the subject such that the thread is pulled into the location previously occupied by the needle. The excess thread is cut from the needle at the skin surface of the subject.

In still other aspects, methods of using threads of hyaluronic acid or salts, hydrates or solvates thereof or threads of cross linked hyaluronic acid or salts, hydrates or solvates thereof or combinations thereof, for example, as dermal fillers, adhesion barriers, wound dressings including negative pressure wound dressings, sutures, etc. is provided. Further provided are methods of using threads of hyaluronic acid or salts, hydrates or solvates thereof or threads of cross linked hyaluronic acid or salts, hydrates or solvates thereof or combinations thereof, for example, in surgery, ophthalmology, wound closure, drug delivery, etc.

BRIEF DESCRIPTION OF THE DRAWINGS

FIG. 1 illustrates a thread attached to the proximal end of a needle, in its entirety;

FIG. 2A illustrates a close-up view of a thread inserted into the inner-diameter of a needle;

FIG. 2B illustrates a close-up view of the proximal end of a solid needle with the thread overlapping the needle;

FIG. 3A illustrates a fine, facial wrinkle in the peri-orbital region of a human;

FIG. 3B illustrates a needle and thread being inserted into the dermis of the wrinkle at the medial margin;

DETAILED DESCRIPTION

Definitions

Figure 3C:
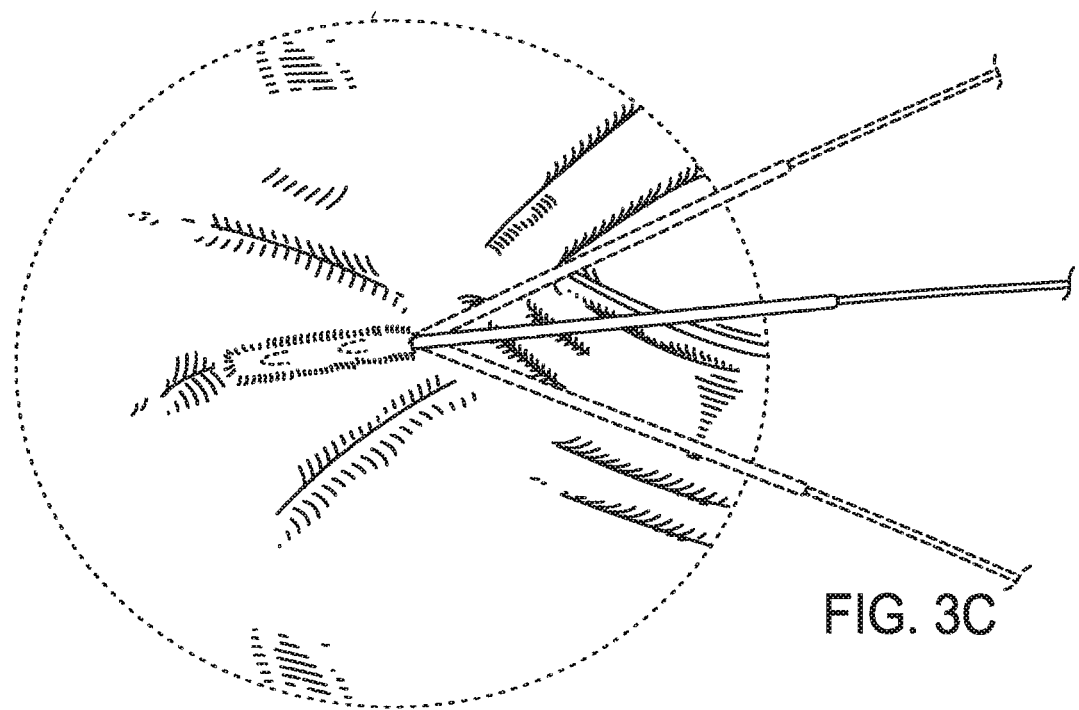
FIG. 3C illustrates the needle being adjusted to traverse beneath the wrinkle.

"Buffer" includes, but is not limited to, 2-amino-2-methyl-1,3-propanediol, 2-amino-2-methyl-1-propanol, L-(+)-tartaric acid, D-(−)-tartaric acid, ACES, ADA, acetic acid, ammonium acetate, ammonium bicarbonate, ammonium citrate, ammonium formate, ammonium oxalate, ammonium phosphate, ammonium sodium phosphate, ammonium sulfate, ammonium tartrate, BES, BICINE, BIS-TRIS, bicarbonate, boric acid, CAPS, CHES, calcium acetate, calcium carbonate, calcium citrate, citrate, citric acid, diethanolamine, EPP, ethylenediaminetetraacetic acid disodium salt, formic acid solution, Gly-Gly-Gly, Gly-Gly, glycine, HEPES, imidazole, lithium acetate, lithium citrate, MES, MOPS, magnesium acetate, magnesium citrate, magnesium formate, magnesium phosphate, oxalic acid, PIPES, phosphate buffered saline, phosphate buffered saline, piperazine potassium D-tartrate, potassium acetate, potassium bicarbonate, potassium carbonate, potassium chloride, potassium citrate, potassium formate, potassium oxalate, potassium phosphate, potassium phthalate, potassium sodium tartrate, potassium tetraborate, potassium tetraoxalate dehydrate, propionic acid solution, STE buffer solution, sodium 5,5-diethylbarbiturate, sodium acetate, sodium bicarbonate, sodium bitartrate monohydrate, sodium carbonate, sodium citrate, sodium formate, sodium oxalate, sodium phosphate, sodium pyrophosphate, sodium tartrate, sodium tetraborate, TAPS, TES, TNT, TRIS-glycine, TRIS-acetate, TRIS buffered saline, TRIS-HCl, TRIS phosphate-EDTA, tricine, triethanolamine, triethylamine, triethylammonium acetate, triethylammonium phosphate, trimethylammonium acetate, trimethylammonium phosphate, Trizma® acetate, Trizma® base, Trizma® carbonate, Trizma® hydrochloride or Trizma® maleate.

"Salt" refers to a salt of hyaluronic acid, which possesses the desired activity of the parent compound. Such salts include, but are not limited to: (1) acid addition salts, formed with inorganic acids such as hydrochloric acid, hydrobromic acid, sulfuric acid, nitric acid, phosphoric acid and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, t-butylacetic acid, lauryl sulfuric acid, gluconic acid, glutamic acid, hydroxynaphthoic acid, salicylic acid, stearic acid, muconic acid and the like; or (2) salts formed when an acidic proton present in the parent compound is replaced by an ammonium ion, a metal ion, e.g., an alkali metal ion (e.g., sodium or potassium), an alkaline earth ion (e.g., calcium or magnesium), or an aluminum ion; or coordinates with an organic base such as ethanolamine, diethanolamine, triethanolamine, N-methylglucamine, morpholine, piperidine, dimethylamine, diethylamine and the like. Also included are salts of amino acids such as arginates and the like, and salts of organic acids like glucurmic or galacturonic acids and the like.

Threads of Hyaluronic Acid and Derivatives Thereof

The present invention generally provides threads of hyaluronic acid or salts, hydrates or solvates thereof, threads of cross linked hyaluronic acid or salts, hydrates or solvates thereof and combinations thereof. In some embodiments, the hyaluronic acid is isolated from an animal source. In other embodiments, the hyaluronic acid is isolated from bacterial fermentation.

In some embodiments, the lifetime of the threads of hyaluronic acid or salts, hydrates or solvates thereof, in vivo is between about 1 minute and about 1 month. In other embodiments, the lifetime of the thread of hyaluronic acid or salts, hydrates or solvates thereof, in vivo is between about 10 minutes and about 1 week. In still other embodiments, the lifetime of the thread of hyaluronic acid or salts, hydrates or solvates thereof, in vivo is between about 1 hour and about 3 days.

In some embodiments, the lifetime of the thread of cross linked hyaluronic acid or salts, hydrates or solvates thereof, in vivo is between about 1 week and about 24 months. In other embodiments, the lifetime of the thread of cross linked hyaluronic acid or salts, hydrates or solvates thereof, in vivo is between about 1 month and about 12 months. In still other embodiments, the lifetime of the thread of hyaluronic acid or salts, hydrates or solvates thereof, in vivo is between about 3 months and about 9 months.

In some embodiments, hyaluronic acid or salts, hydrates or solvates thereof have been cross linked with butanediol diglycidyl ether (BDDE), divinyl sulfone (DVS) or 1-ethyl-3-(3-dimethylaminopropyl) carbodiimide hydrochloride (EDC). Those of skill in the art will appreciate that many other cross linking agents may be used to crosslink hyaluronic acid or salts, hydrates or solvates thereof.

Accordingly, the above list of cross linking agents is illustrative rather than comprehensive.

In some of the above embodiments, the degree of cross linking between hyaluronic acid or salts, hydrates or solvates thereof and the cross linking agent is between about 0.01% and about 20%. In other of the above embodiments, the degree of cross linking between hyaluronic acid or salts, hydrates or solvates thereof and the cross linking agent is between about 0.1% and about 10%. In still other of the above embodiments, the degree of cross linking between hyaluronic acid or salts, hydrates or solvates thereof and the cross linking agent is between about 1% and about 8%.

In some of the above embodiments, the thread includes one or more therapeutic or diagnostic agents. In other of the above embodiments, the diagnostic agent is soluble TB (tuberculosis) protein. In still other of the above embodiments, the therapeutic agent is an anesthetic, including but not limited to, lidocaine, xylocaine, novocaine, benzocaine, prilocaine, ropivacaine, propofol or combinations thereof. In still other of the above embodiments, the therapeutic agent is epinephrine, adrenaline, ephedrine, aminophylline, theophylline or combinations thereof. In still other of the above embodiments, the therapeutic agent is botulism toxin. In still other of the above embodiments, the therapeutic agent is laminin-511. In still other of the above embodiments, the therapeutic agent is glucosamine, which can be used, for example, in the treatment of regenerative joint disease. In still other of the above embodiments, the therapeutic agent is an antioxidant, including but not limited to, vitamin E or all-trans retinoic acid such as retinol. In still other of the above embodiments, the therapeutic agent includes stem cells. In still other of the above embodiments, the therapeutic agent is insulin, a growth factor such as, for example, NGF (nerve growth factor), BDNF (brain-derived neurotrophic factor), PDGF (platelet-derived growth factor) or Purmorphamine Deferoxamine NGF (nerve growth factor), dexamethasone, ascorbic acid, 5-azacytidine, 4,6-disubstituted pyrrolopyrimidine, cardiogenols, cDNA, DNA, RNAi, BMP-4 (bone morphogenetic protein-4), BMP-2 (bone morphogenetic protein-2), an antibiotic agent such as, for example, β lactams, quinolones including fluoroquinolones, aminoglycosides or macrolides, an anti-fibrotic agent, including but not limited to, hepatocyte growth factor or Pirfenidone, an anti-scarring agent, such as, for example, anti-TGF-b2 monoclonal antibody (rhAnti-TGF-b2 mAb), a peptide such as, for example, GHK copper binding peptide, a tissue regeneration agent, a steroid, fibronectin, a cytokine, an analgesic such as, for example, Tapentadol HCl, opiates, (e.g., morphine, codone, oxycodone, etc.) an antiseptic, alpha- beta or gamma-interferon, EPO, glucagons, calcitonin, heparin, interleukin-1, interleukin-2, filgrastim, a protein, HGH, luteinizing hormone, atrial natriuretic factor, Factor VIII, Factor IX, or a follicle-stimulating hormone. In still other of the above embodiments, the thread contains a combination of more than one therapeutic agent or diagnostic agent. In some of these embodiments, different threads comprise different therapeutic agents or diagnostic agents.

In some of the above embodiments, the thread has an ultimate tensile strength of between about 0 kpsi and about 250 kpsi. In other of the above embodiments, the thread has an ultimate tensile strength of between about 1 kpsi and about 125 kpsi. In still other of the above embodiments, the thread has an ultimate tensile strength of between about 5 kpsi and about 100 kpsi.

In some of the above embodiments, the thread has an axial tensile strength of between about 0.01 lbs and about 10 lbs. In other of the above embodiments, the thread has an axial tensile strength of between about 0.1 lbs and about 5 lbs. In still other of the above embodiments, the thread has an axial tensile strength of between about 0.5 lbs and about 2 lbs.

In some of the above embodiments, the thread has a cross-section area of between about $1*10^6$ in$^2$ and about $1,000*10^6$ in$^2$. In other of the above embodiments, the thread has a cross-section area of between about $10*10^6$ in$^2$ and about $500*10^6$ in$^2$. In still other of the above embodiments, the thread has a cross-section area of between about $50*10^6$ in$^2$ and about $250*10^6$ in$^2$.

In some of the above embodiments, the thread has a diameter of between about 0.0001 in and about 0.100 in. In other of the above embodiments, the thread has a diameter of between about 0.001 in and about 0.020 in. In still other of the above embodiments, the thread has a diameter of between about 0.003 and about 0.010 in.

In some of the above embodiments, the thread has an elasticity of between about 1% and 200%. In other of the above embodiments, the thread has an elasticity of between about 5% and about 100%. In still other of the above embodiments, the thread has an elasticity of between about 10% and 50%. Herein, elasticity is the % elongation of the thread while retaining ability to return to the initial length of the thread.

In some of the above embodiments, the thread has a molecular weight of between about 0.1 MD and about 8 MD (MD is a million Daltons). In other of the above embodiments, the thread has a molecular weight of between about 0.5 MD to about 4 MD. In still other of the above embodiments, the thread has a molecular weight of between about 1 MD to about 2 MD.

In some of the above embodiments, the thread has a persistent chain length of between about 10 nm and about 250 nm. In other of the above embodiments, the thread has a persistent chain length of between about 10 nm and about 125 nm. In still other of the above embodiments, the thread has a persistent chain length of between about 10 nm and about 75 nm.

In some of the above embodiments, the cross-sectional area of the thread when fully hydrated swells to between about 0% to about 10,000%. In other of the above embodiments, the cross-sectional area of the thread when fully hydrated swells to between about 0% to about 2,500%. In still other of the above embodiments, the cross-sectional area of the thread when fully hydrated swells to between about 0% to about 900%.

In some of the above embodiments, the thread elongates when fully hydrated to between about 0% to about 1,000%. In other of the above embodiments, the thread elongates when fully hydrated to between about 0% to about 100%. In still other of the above embodiments, the thread elongates when fully hydrated to between about 0% to about 30%.

In some of the above embodiments, the thread is fully hydrated after submersion in an aqueous environment in between about 1 second and about 24 hours. In other of the above embodiments, the thread is fully hydrated after submersion in an aqueous environment in between about 1 second and about 1 hour. In still other of the above embodiments, the thread is fully hydrated after submersion in an aqueous environment in between about 1 second to about 5 minutes.

In some embodiments, the thread is cross linked and has an ultimate tensile strength of between about 50 kpsi and about 75 kpsi, a diameter of between 0.005 in and about 0.015 in, the thickness or diameter of the thread when fully hydrated swells between about 50% to about 100% and the lifetime of the thread in vivo is about 6 months.

In some embodiments, braids may be formed from the threads described above. In other embodiments, cords may be formed from the threads described above. In still other embodiments, a woven mesh may be formed from the threads described above. In still other embodiments, a woven mesh may be formed from the braids or cords described above.

In some embodiments, a three-dimensional structure may be constructed by weaving or wrapping or coiling or layering the threads described above. In other embodiments, a three-dimensional structure may be constructed by weaving or wrapping or coiling or layering the braids described above. In still other embodiments, a three-dimensional structure may be constructed by weaving or wrapping or coiling or layering the cords described above. In still other embodiments, a three-dimensional structure may be constructed by weaving or wrapping or coiling or layering the meshes described above.

In some embodiments, a three-dimensional, cylindrical implant is made of any of the threads is provided. An exemplary use for such an implant is for nipple reconstruction. In some embodiments, the threads used to make the cylindrical implant are cross linked and include chondrocyte adhesion compounds. In other embodiments, the cylindrical shape is provided by multiple, concentric coils of threads.

Threads of hyaluronic acid and/or derivatives thereof may contain one or more chiral centers and therefore, may exist as stereoisomers, such as enantiomers or diastereomers. In general, all stereoisomers (i.e., all possible enantiomers and stereoisomers of the illustrated compounds including the stereoisomerically pure form (e.g., enantiomerically pure or diastereomerically pure) and enantiomeric and stereoisomeric mixtures are within the scope of the present invention.

Threads of hyaluronic acid and/or derivatives thereof may exist in several tautomeric forms and mixtures thereof all of which are within the scope of the present invention. Threads of hyaluronic acid and/or derivatives thereof may exist in unsolvated forms as well as solvated forms, including hydrated forms. In general, hydrated and solvated forms are within the scope of the present invention. Accordingly, all physical forms of threads of hyaluronic acid and/or derivatives thereof are equivalent for the uses contemplated by the present invention and are intended to be within the scope of the present invention.

Methods of Making Threads of Hyaluronic Acid and Derivatives Thereof

The present invention also provides methods for making threads of hyaluronic acid and derivatives thereof as described above. In some embodiments, a method of making threads of hyaluronic acid or salts, hydrates or solvates thereof, is provided Hyaluronic acid or salts, hydrates or solvates thereof are mixed with water or a buffer to form a gel. The gel is then extruded to form a thread of gel. The gel can be extruded, for example, by placing the gel in a syringe with a nozzle, pressurizing the syringe, and linearly translating the syringe as gel is extruded from the nozzle. Nozzle characteristics such as taper, length and diameter, the syringe pressure, and the speed of linear translation may be adjusted to make threads of different sizes and mechanical characteristics. Another method of making a thread of gel is by rolling the gel, i.e., like dough, or by placing it into a mold. Still another method of making a thread of gel is to allow the gel to stretch into a thread under the influence of gravity or using centrifugal force. Still another method of making a thread of gel is by shearing the gel in between charged parallel glass plates. Yet another method of making a thread of gel is by confining the gel into a groove patterned on an elastomer and then stretching the elastomer. Yet another method of making a thread of gel is by confining the gel into a permeable tubular structure that allows dehydration of the thread, and if necessary controlling the nature of the dehydration by adjusting environmental parameters such as temperature, pressure and gaseous composition. The thread of hyaluronic acid or salts, hydrates or solvates thereof is then dried after preparation.

In other embodiments, a method of making threads of cross linked hyaluronic acid or salts, hydrates or solvates thereof, is provided. Hyaluronic acid or salts, hydrates or solvates thereof are mixed with water or a buffer and a cross linking agent to form a gel. The gel is then extruded to form a thread as described above or the thread can be made by any of the methods described above. Generally, the gel should be extruded or otherwise manipulated soon after addition of the cross linking agent so that cross linking occurs as the thread dries. The thread of cross linked hyaluronic acid or salts, hydrates or solvates thereof is then dried after preparation.

In some embodiments, the ratio of cross linking agent to hyaluronic acid is between about 0.01% and about 10%. In other embodiments, the ratio of cross linking agent to hyaluronic acid is between about 0.02% and about 5%. In still other embodiments, the ratio of cross linking agent to hyaluronic acid is between about 0.1% and about 3%.

In some of the above embodiments, one or more therapeutic or diagnostic agents are included in the gel forming step.

In some of the above embodiments, the gel has a concentration by weight of hyaluronic acid of between about 0.1% and about 10%. In other of the above embodiments, the gel has a concentration by weight of hyaluronic acid of between about 1% and about 7%. In still other of the above embodiments, the gel has a concentration by weight of hyaluronic acid of between about 4% and about 6%.

In some of the above embodiments, the polymer chains are further oriented along the axis of the thread by being stretched axially. In other of the above embodiments, the polymer chains are oriented along the axis of the thread by gravimetric force or centrifugal force. In still other of the above embodiments, gravimetric force is applied by hanging the thread vertically. In still other of the above embodiments, the polymer chains are oriented along the axis of the thread by application of an electric potential along the length of the thread. In still other of the above embodiments, the polymer chains are oriented along the axis of the thread by a combination of the above methods.

In some of the above embodiments, the threads are hydrated with water and then dried again. In other of the above embodiments, the hydration and drying steps are repeated multiple times. In still other of the above embodiments, the polymer chains are oriented along the axis of the thread by being stretched axially, by application of gravimetric force or centrifugal force, by application of an electric potential along the length of the thread or by combinations thereof. In still other of the above embodiments, a therapeutic agent or a diagnostic agent or a cross linking agent is applied to the thread during the hydration step.

In some of the above embodiments, the gel is extruded over a previously made thread to provide a layered thread.

In another of the above embodiments, after the drying step, the thread is submerged or rinsed with an agent. In some of the above embodiments, the agent is a cross linking agent, therapeutic or diagnostic agent.

In another of the above embodiments, while the thread is hydrated, for example after a rinsing step, the thread is submerged or rinsed with an agent. In some of the above embodiments, the agent is a cross linking agent, therapeutic or diagnostic agent.

In still other of the above embodiments, the thread is frozen and then thawed. In still other of the above embodiments, the thread is frozen and then thawed at least more than once.

In still other of the above embodiments, a dried thread is irradiated to promote cross linking. In some of the above embodiments, a hydrated thread is irradiated to promote cross linking.

In still other of the above embodiments, a dried or hydrated thread is coated to alter the properties of the thread, with a bioabsorbable biopolymer, such as for example, collagen, PEG or PLGA. Alternatively, woven constructs, whether single layer or 3D, can be coated in their entirety to create weaves or meshes with altered physical properties from that of a free-woven mesh.

Methods of Using Threads of Hyaluronic Acid and Derivatives Thereof

The threads, braids, cords, woven meshes or three-dimensional structures described herein can be used, for example, to fill aneurysms, occlude blood flow to tumors, (i.e., tumor occlusion), in eye-lid surgery, in penile augmentation (e.g., for enlargement or for sensitivity reduction, i.e., pre-mature ejaculation treatment), inter-nasal (blood-brain barrier) delivery devices for diagnostic and/or therapeutic agents, corneal implants for drug delivery, nose augmentation or reconstruction, lip augmentation or reconstruction, facial augmentation or reconstruction, ear lobe augmentation or reconstruction, spinal implants (e.g., to support a bulging disc), root canal filler (medicated with therapeutic agent), glottal insufficiency, laser photo-refractive therapy (e.g., hyaluronic acid thread/weave used as a cushion), scaffolding for organ regrowth, spinal cord treatment (BDNF and NGF), in Parkinson's disease (stereotactic delivery), precise delivery of therapeutic or diagnostic molecules, in pulp implantation, replacement pulp root canal treatment, shaped root canal system, negative pressure wound therapy, adhesion barriers and wound dressings.

In some embodiments, the threads, braids, cords, woven meshes or three-dimensional structures described herein are used as dermal fillers in various aesthetic applications. In other embodiments, the threads, braids, cords, woven meshes or three-dimensional structures described herein are used as sutures in various surgical applications. In still other embodiments, the threads, braids, cords, woven meshes or three-dimensional structures described herein are used in ophthalmologic surgery, drug delivery and intra-articular injection.

In some embodiments, the threads, braids, cords, woven meshes or three-dimensional structures described herein are used in wound dressings including negative pressure wound dressings.

In some embodiments, wound dressing remains in contact with the wound for at least 72 hours. In other embodiments, the negative pressure wound dressing remains in contact with the wound for at least 1 week. In still other embodiments, the wound dressing remains in contact with the wound for at least 2 weeks. In still other embodiments, the wound dressing remains in contact with the wound for at least 3 weeks. In still other embodiments, the wound dressing remains in contact with the wound for at least 4 weeks. In the above embodiments, it should be understood that granulation tissue is not retaining the threads, braids, cords, woven meshes or three-dimensional structures described herein as these components are fully absorbable. In some of these embodiments, the wound dressing is between about 1 cm and about 5 cm thick. Accordingly, in some of these embodiments, wound bed closure may be achieved without changing the dressing.

In some embodiments, the woven meshes described herein are used in wound dressings including negative pressure wound dressings. In other embodiments, the dressing include between 2 and about 10 layers of woven meshes.

In still other embodiments, the woven meshes comprise identical threads. In still other embodiments, the woven meshes comprise different threads.

In some embodiments, the woven meshes are between about 1 mm and about 2 mm thick when dry. In other embodiments, the woven meshes are between about 2 mm and about 4 mm thick when dry.

In some embodiments, the pore size of the woven mesh is between about 1 mm and about 10 mm in width. In other embodiments, the pore size of the woven mesh is between about 0.3 mm and about 0.6 mm in width. In still other embodiments, the pores of the woven mesh are aligned. In still other embodiments, the pores of the woven mesh are staggered. In still other embodiments, the woven meshes are collimated to create pores of desired size.

In some embodiments, the woven mesh is mechanically stable at a vacuum up to about 75 mm Hg. In other embodiments, the woven mesh is mechanically stable at a vacuum up to about 150 mm Hg.

In some embodiments, the woven mesh includes collagen. In other embodiments, the dressing is attached to a polyurethane foam. In still other embodiments, the polyurethane foam is open celled. In still other embodiments, the dressing is attached to a thin film. In still other embodiments, the thin film is silicone or polyurethane. In still other embodiments, the dressing is attached to the thin film with a water soluble adhesive.

In some embodiments, the thread used in the dressing includes a therapeutic agent or a diagnostic agent.

In some embodiments, a negative pressure wound dressing (Johnson et al., U.S. Pat. No. 7,070,584, Kemp et al., U.S. Pat. No. 5,256,418, Chatelier et al., U.S. Pat. No. 5,449,383, Bennet et al., U.S. Pat. No. 5,578,662, Yasukawa et al., U.S. Pat. Nos. 5,629,186 and 5,780,281 and Ser. No. 08/951,832) is provided for use in vacuum induced healing of wounds, particularly open surface wounds (Zamierski U.S. Pat. Nos. 4,969,880, 5,100,396, 5,261,893, 5,527,293 and 6,071,267 and Argenta et al., U.S. Pat. Nos. 5,636,643 and 5,645,081). The dressing includes a pad which conforms to the wound location, an air-tight seal which is removably adhered to the pad, a negative pressure source in fluid communication with the pad and the threads, braids, cords, woven meshes or three-dimensional structures described herein attached to the wound contacting surface of the pad. The pad, seal and vacuum source are implemented as described in the prior art.

In other embodiments, the threads, braids, cords, woven meshes or three-dimensional structures described herein are mechanically stable at a vacuum up to about 75 mm Hg. In still other embodiments, the threads, braids, cords, woven meshes or three-dimensional structures described herein are mechanically stable at a vacuum up to about 150 mm Hg. In still other embodiments, the dressing includes at least one layer of woven mesh. In still other embodiments, the dressing include between 2 and about 10 layers of woven mesh. In still other embodiments, the pad is a foam. In still other embodiments, the pad is an open cell polyurethane foam.

In some embodiments a tube connects the pad to the negative pressure source. In still other embodiments, a removable canister is inserted between the pad and the negative pressure source and is in fluid communication with both the pad and the negative pressure source.

In some embodiments, the threads, braids, cords, woven meshes or three-dimensional structures described herein are not hydrated. Accordingly, in these embodiments, the dressing could absorb wound exudates when placed in contact with the wound. In other embodiments, the threads, braids, cords, woven meshes or three-dimensional structures described herein are hydrated. Accordingly, in these embodiments, the dressing could keep the wound moist when placed in contact with the wound.

In some embodiments, an input port attached to a fluid is connected with the pad. Accordingly, in these embodiments, fluid could be dispensed in the wound. In some embodiments, the fluid is saline. In other embodiments, the fluid contains diagnostic or therapeutic agents.

In some embodiments, the threads, braids, cords, woven meshes or three-dimensional structures described herein are used as adhesion barriers. In some embodiments, the woven meshes described herein are used in adhesion barriers.

Figure 3D:
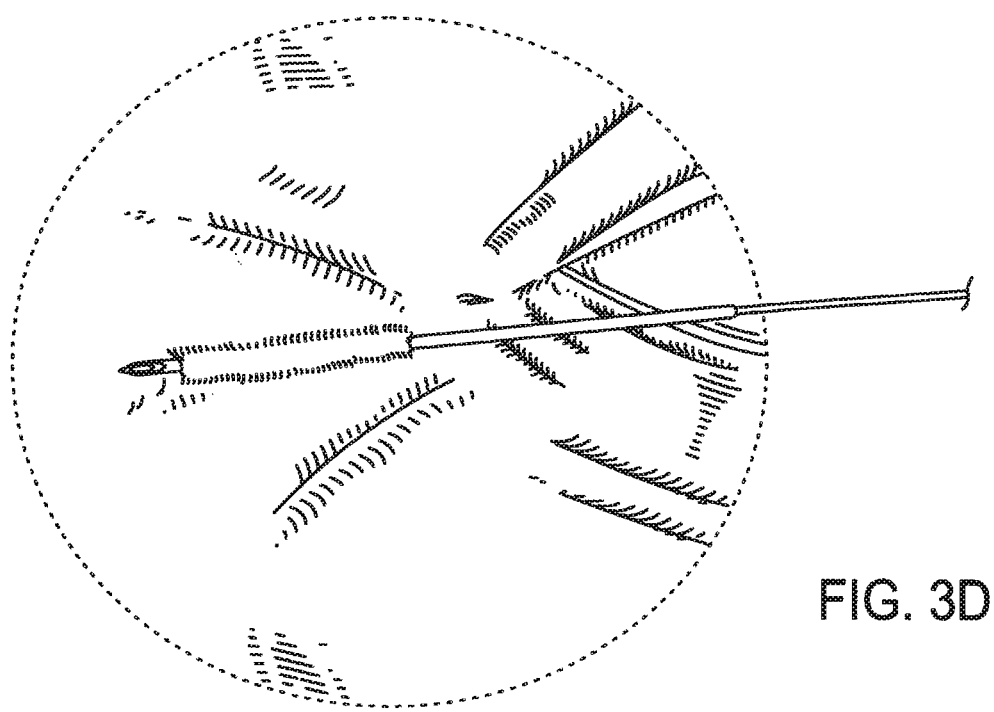
FIG. 3D illustrates the needle exiting at the lateral margin of the wrinkle.
Figure 3E:
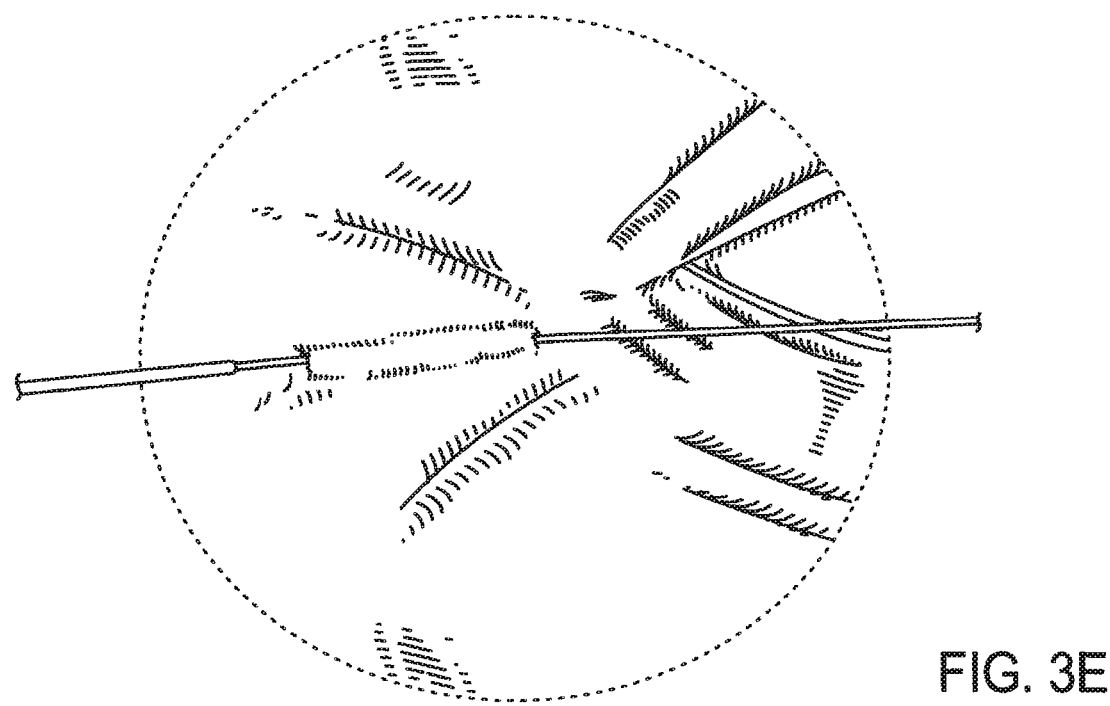
FIG. 3E illustrates the needle having pulled the thread into the location it previously occupied beneath the wrinkle.
Figure 3F:
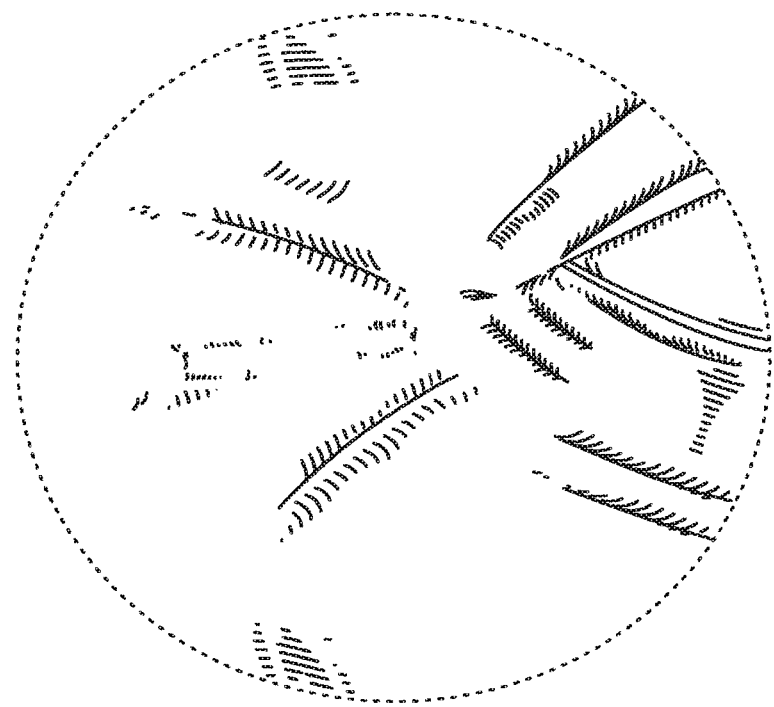
FIG. 3F illustrates the thread implanted beneath the wrinkle, with excess thread having been cut off.

In some embodiments, a method of treating a wrinkle in a subject is provided. For example, the wrinkle may be in the peri-orbital region as illustrated in FIG. 3A. The thread may be attached to a needle as illustrated, for example, in FIGS. 1, 2A and 2B. The distal end of the needle may be inserted through the skin surface of the subject into the dermis adjacent to or within the wrinkle as illustrated, for example, in FIG. 3B. In some embodiments, the thread is inserted into the subcutaneous space instead of the dermis. The needle then may traverse the dermis of the subject beneath the wrinkle as illustrated, for example, in FIG. 3C. The needle then may exit the skin of the subject at the opposite margin of the wrinkle, as illustrated, for example, in FIG. 3D. The needle may then be pulled distally until it is removed from the subject such that the thread is pulled into the location previously occupied by the needle beneath the wrinkle, as illustrated, for example, in FIG. 3E. Finally, excess thread is cut from the needle at the skin surface of the subject which leaves the thread implanted as illustrated, for example, in FIG. 3F.

Figure 5A:
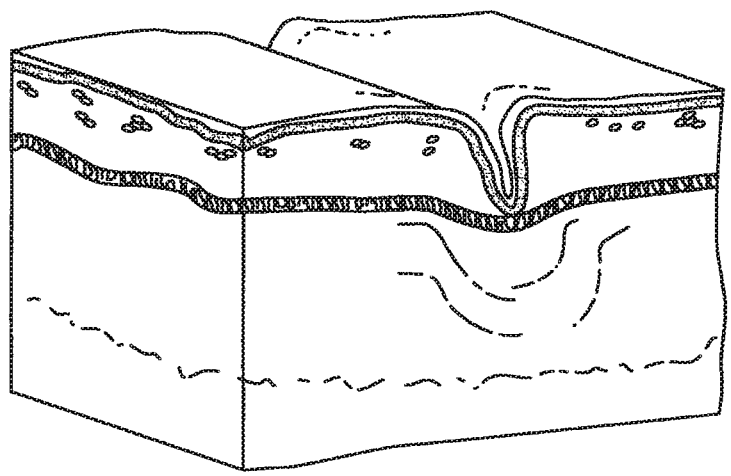
FIG. 5A illustrates a cross-sectional view of a fold or a wrinkle.
Figure 5B:
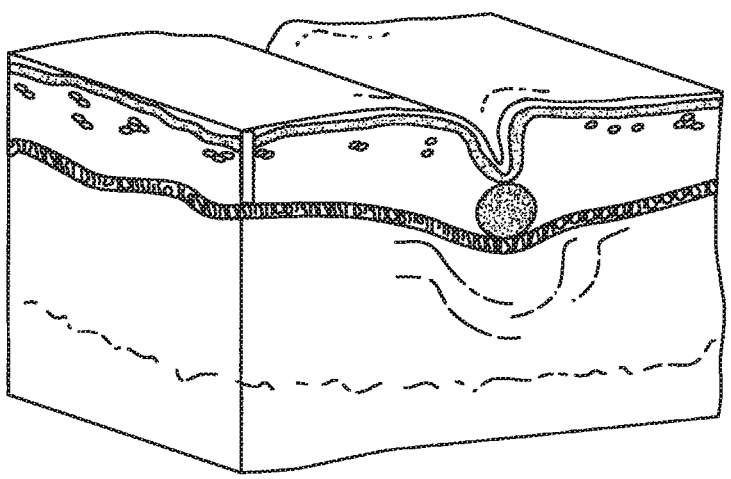
FIG. 5B illustrates a thread implanted beneath a wrinkle that is not yet hydrated.
Figure 5C:
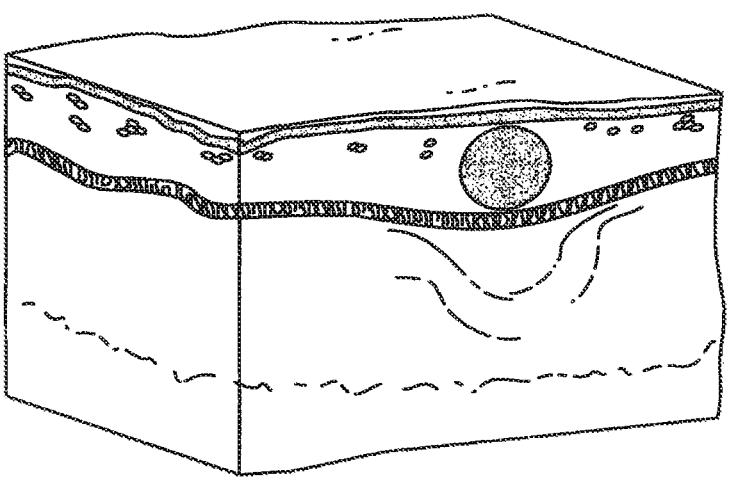
FIG. 5C illustrates a thread implanted beneath a wrinkle that is fully hydrated and has flattened the surface appearance of the wrinkle.

While not wishing to be bound by theory, the method above may successfully treat wrinkles as shown in FIGS. 5A, 5B and 5C. A typical wrinkle is illustrated in FIG. 5A. FIG. 5B illustrates a thread implanted beneath a wrinkle that is not yet hydrated. As the thread implanted beneath the wrinkle becomes fully hydrated the surface appearance of the wrinkle is concurrently flattened as illustrated in FIG. 5C.

In some embodiments, the above method may be used to rejuvenate the skin of a subject in need thereof. In many of these embodiments, the thread includes substantial amounts of non-cross linked hyaluronic acid. In some of these embodiments, the thread includes antioxidants, vitamin E or retinol or combinations thereof.

Figure 4A:
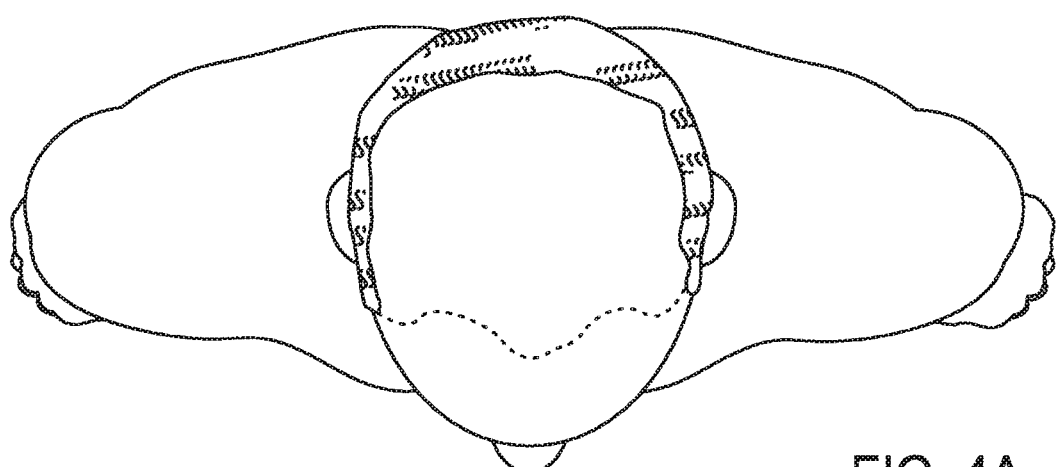
FIG. 4A illustrates a top-down view of a male with typical male-pattern baldness.
Figure 4B:
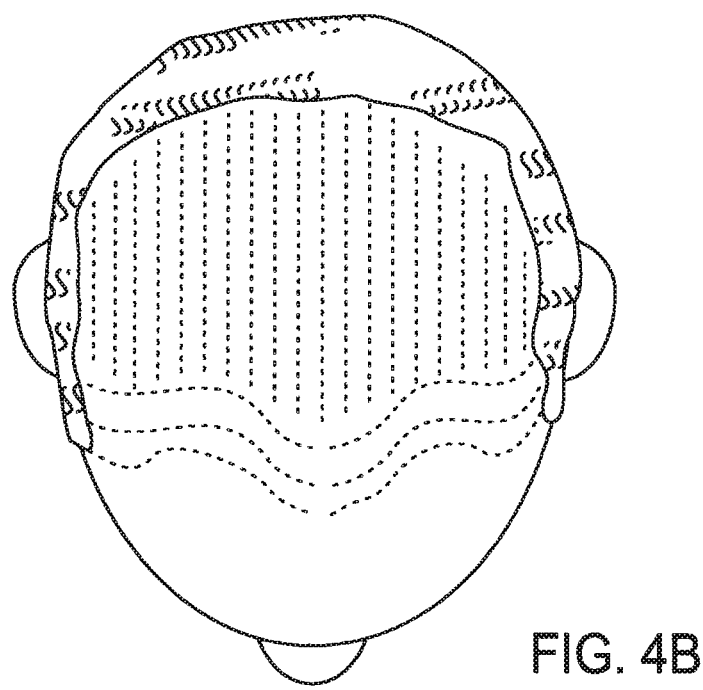
FIG. 4B illustrates where hair re-growth is desired, taking hair-lines into consideration.
Figure 4C:
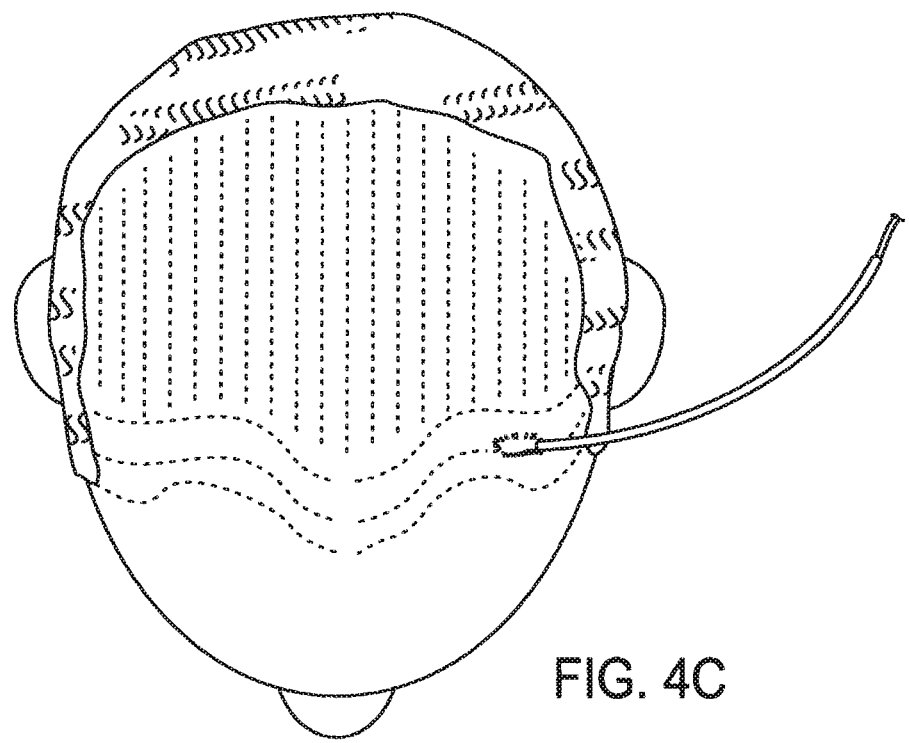
FIG. 4C illustrates a curved needle with attached thread being inserted into one imaginary line where hair re-growth is desired.
Figure 4D:
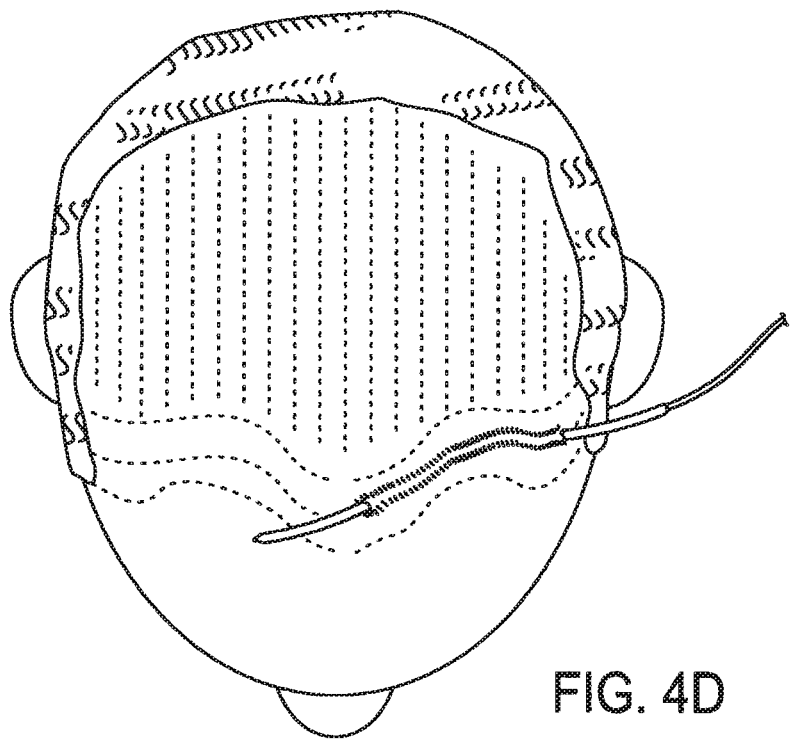
FIG. 4D illustrates the needle traversing the imaginary line, and exiting the skin.
Figure 4E:
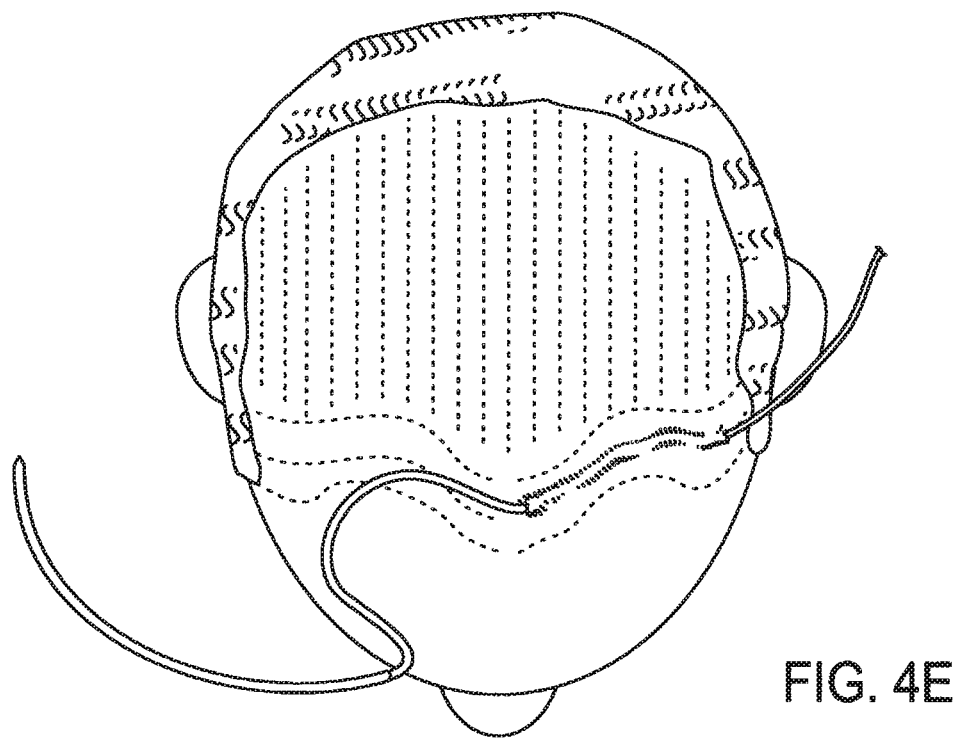
FIG. 4E illustrates the needle pulled through distally, pulling along the thread into the desired location.
Figure 4F:
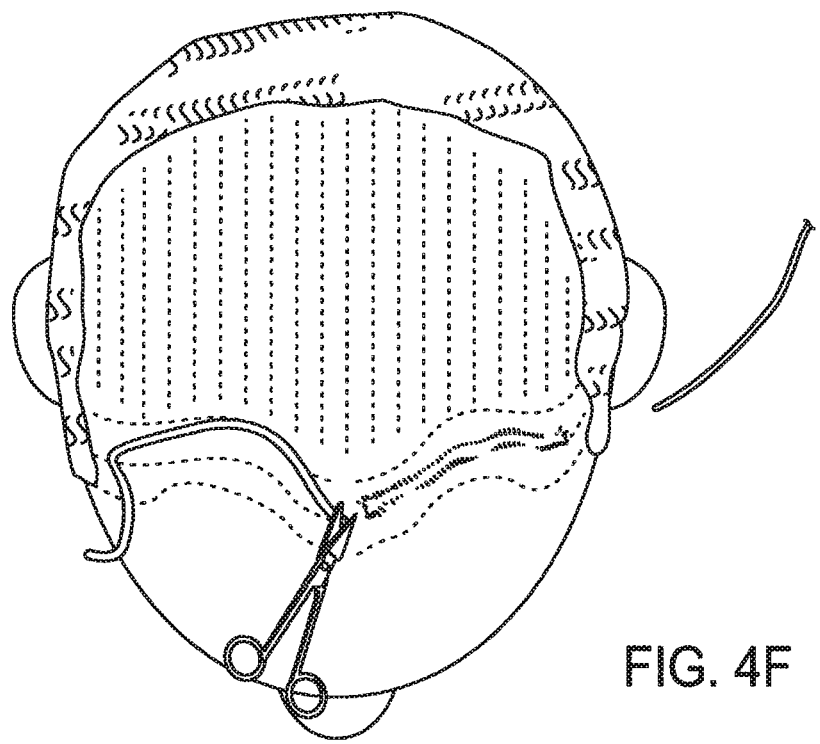
FIG. 4F illustrates scissors being used to cut excess thread.

In some embodiments, a method of treating hair loss in a subject is provided. A subject such as, for example, a male with typical male-pattern baldness is illustrated in FIG. 4A and the area where hair growth (with imaginary hairlines) is desired is shown in FIG. 4B. The thread may be attached to a needle as illustrated, for example, in FIGS. 1, 2A, 2B and 4C. The distal end of the needle may be inserted into one of the hair lines as illustrated, for example, in FIG. 4C. The needle then may traverse the area beneath the hairline of the subject and then may exit the skin of the subject as illustrated, for example, in FIG. 4D. The needle may then be pulled distally until it is removed from the subject such that the thread is pulled into the location previously occupied by the needle as illustrated, for example, in FIG. 4E. Finally, excess thread is cut from the needle at the skin surface of the subject which leaves the thread implanted as illustrated, for example, in FIG. 4D.

In some embodiments, a method for treating tumors in a subject in need thereof is provided. The thread may be attached to a needle as illustrated, for example, in FIGS. 1, 2A and 2B. The distal end of the needle may be inserted into the tumor of the subject. The needle then may traverse the tumor and then may exit the tumor. The needle may then be pulled distally until it is removed from the tumor of the subject such that the thread is pulled into the location previously occupied by the needle. Finally, excess thread is cut from the needle which leaves the thread implanted in the tumor of the subject. In some of the above embodiments, the thread includes an anti-cancer agent. In some embodiments, the thread is cross linked and includes Bcl-2 inhibitors.

Figure 6A:
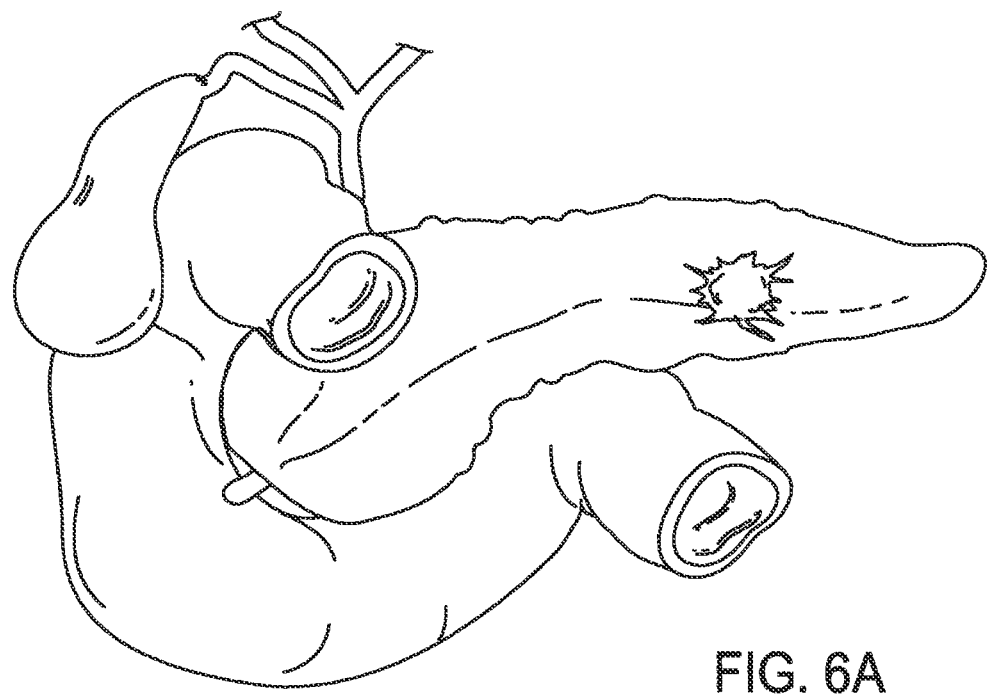
FIG. 6A illustrates a human pancreas with a tumor.
Figure 6B:
FIG. 6B illustrates a curved needle with a thread attached thereto.
Figure 6C:
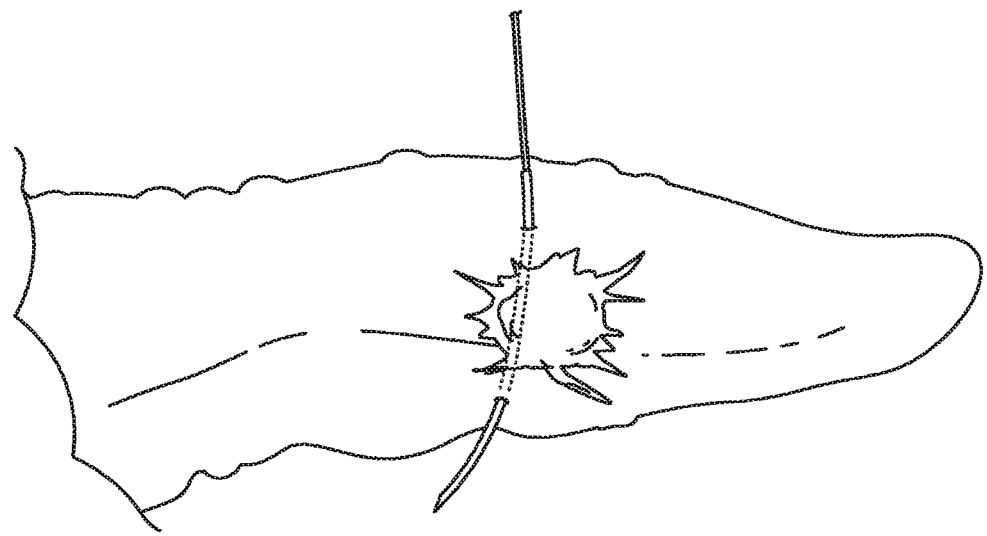
FIG. 6C illustrates a curved needle traversing the tumor within the pancreas.
Figure 6D:
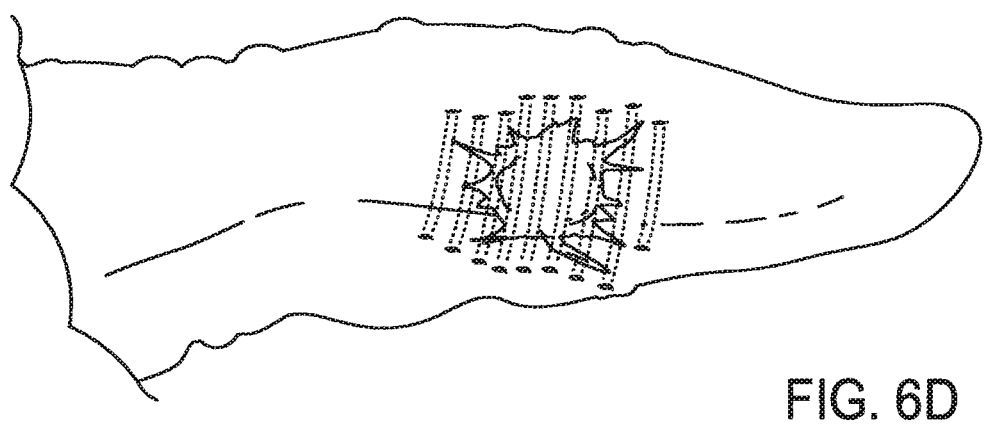
FIG. 6D illustrates the end-result of repeated implantations of thread.

In an exemplary embodiment, methods of the current invention may be used to treat pancreatic tumors. FIG. 6A illustrates a human pancreas with a tumor while FIG. 6B illustrates a needle with a thread attached thereto. The pancreas may be accessed by surgery or minimally invasively methods such as by laparoscopy. The distal end of the needle may be inserted into the pancreatic tumor. The needle then may traverse the pancreatic tumor as illustrated in FIG. 6C and then may exit the tumor. The needle may then be pulled distally until it is removed from the pancreatic tumor such that the thread is pulled into the location previously occupied by the needle. Finally, excess thread is cut from the needle which leaves the thread implanted in the pancreatic tumor. The process may be repeated any number of times to provide, as illustrated in FIG. 6D, a pancreatic tumor which has been implanted with a number of threads. In some embodiments, the thread includes an anti-cancer agent.

In some embodiments, a method for treating a varicose vein in subject in need thereof is provided. The thread may be attached to a needle as illustrated, for example, in FIGS. 1, 2A and 2B. The distal end of the needle may be inserted into the varicose vein of the subject. The needle then may traverse the varicose vein and then may exit the vein. The needle may then be pulled distally until it is removed from the varicose vein of the subject such that the thread is pulled into the location previously occupied by the needle. Finally, excess thread is cut from the needle which leaves the thread implanted in the varicose vein of the subject. In some embodiments, the needle is a flexible. In other embodiments, the thread coils when hydrated, more readily occluding the vessel.

Figure 7A:
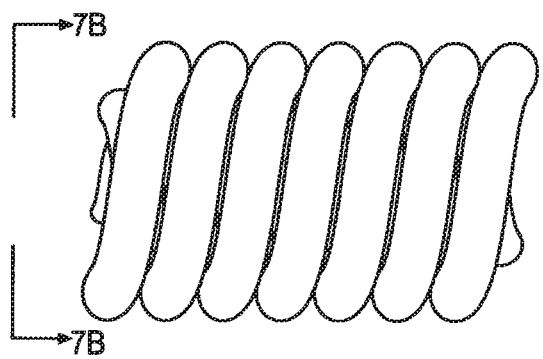
FIG. 7A illustrates multiple layers of concentric coils of thread, shaped to represent a human nipple.
Figure 7B:
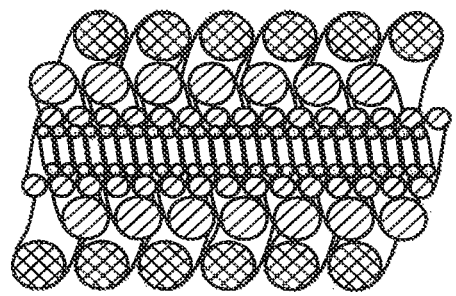
FIG. 7B illustrates the implant of FIG. 7A in cross-section.
Figure 7C:
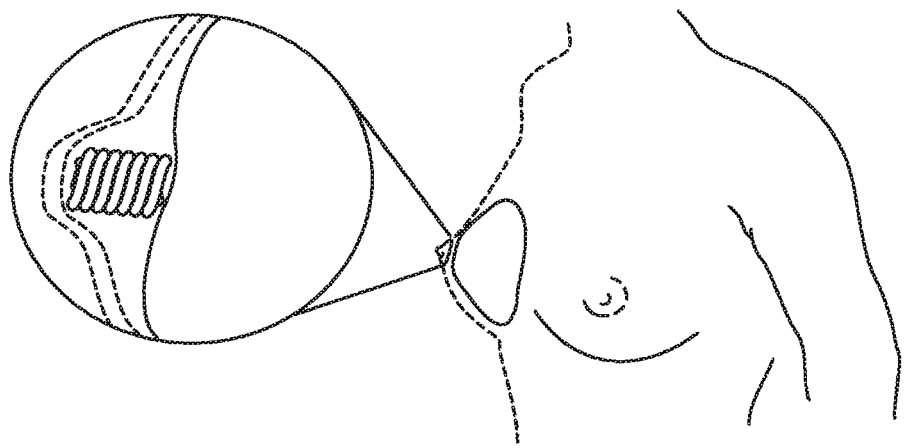
FIG. 7C illustrates how an implant of coiled thread would be used for nipple reconstruction.

In some embodiments, a method for nipple reconstruction is provided where a three-dimensional, cylindrical implant comprised of cross linked threads is implanted underneath the skin. The implant may include therapeutic agents, for example chondrocyte adhesion compounds. FIG. 7A illustrates an implant of multiple layers of concentric coils of threads shaped to represent a nipple while FIG. 7B shows a cross-section of the implant of FIG. 7A. FIG. 7C illustrates how the implant of FIG. 7A could be used for nipple reconstruction.

Figure 8:
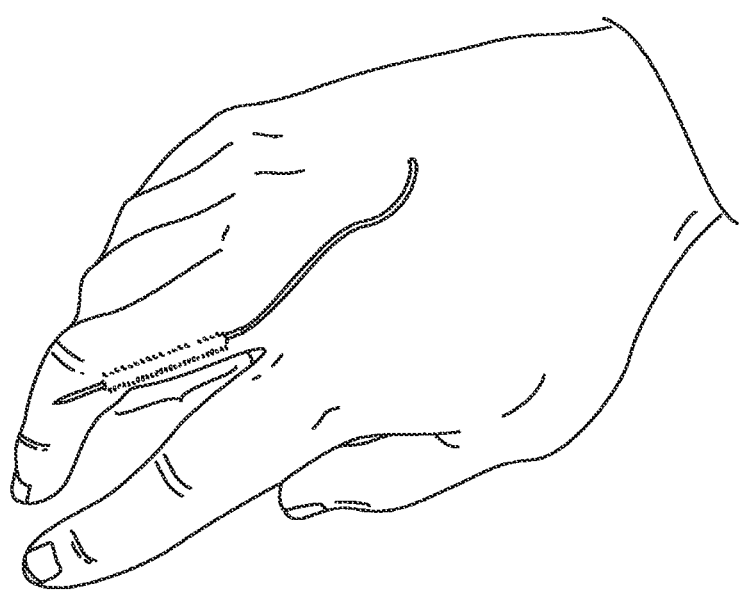
FIG. 8 illustrates how a needle and thread could be used to place a thread in a specific, linear location to promote nerve or vessel regrowth in a specific line.

In some embodiments, methods for nerve or vessel regrowth are provided. As illustrated in FIG. 8, a needle can be used to place a thread in a specific line which could promote nerve or vessel regeneration.

EXAMPLES

The present invention is further defined by reference to the following examples. It will be apparent to those skilled in the art that many modifications, both to materials and methods, may be practiced without departing from the scope of the current invention.

Example 1

Synthesis of a Cross Linked Thread

A cross linked thread of a diameter between 0.004 in and 0.006 in was made by forming a gel with a concentration of 5% hyaluronic acid and 0.4% BDDE, by weight with the remainder comprised of water. A tapered tip nozzle with an inner diameter of 0.02 in, a syringe pressure of 20 psi and a linear translation speed commensurate with the speed of gel ejection from the syringe was used to extrude the gel into a thread form. However, numerous combinations of extrusion parameters that can make a thread of the desired thickness exist. The thread was dried and then rinsed with water which hydrated the thread, which was then stretched during drying. Over the course of multiple rinsing and drying cycles the overall length of the thread was increased by between about 25% and about 100%. The thread made as described above will fail at a tensile force of about between about 0.25 kg and about 1.50 kg and will swell in diameter by about 25% and about 100% when hydrated. It may persist as a thread in vivo between 1 and 9 months.

Example 2

Treatment of Wrinkles of a Cadaver with Hyaluronic Acid Threads

Hypodermic needles (22 to 25 Ga) were affixed with single or double strands of hyaluronic acid threads, ranging from thicknesses of 0.004 in to 0.008 in. Both non-cross-linked threads and threads crosslinked using BDDE were used. The needles were able to traverse wrinkles in a cadaveric head of a 50 y/o woman such as the naso-labial fold, peri-orals, peri-orbitals, frontalis (forehead), and glabellar. The needle was able to pull the thread through the skin such that the thread was located where the needle was previously inserted.

Example 3

Placement of Hyaluronic Acid Threads in Dogs

Acute and chronic canine studies were performed. Hypodermic needles (22 to 25 Ga) were affixed with single or double strands of hyaluronic acid threads, ranging from thicknesses of 0.004 in to 0.008 in. Both non-crosslinked threads and threads cross linked using BDDE were used. In all cases, the needle was able to pull the attached thread or threads into the dermis. Within minutes most threads produced a visible impact on the skin surface of the animals in the form of a linear bump.

Example 4

Comparison of Tensile Strength of Different Hyaluronic Acid Threads

The tensile strength of an autocrosslinked thread of hyaluronic acid was compared to a thread cross linked using the method of Example 1. A thread of non-crosslinked hyaluronic acid was repeatedly frozen and thawed, replicating a method of autocrosslinking hyaluronic acid (Ref. U.S. Pat. No. 6,387,413). All such samples had less tensile force at failure than a thread made using the same extrusion parameters and cross-linked using BDDE as described above.

Finally, it should be noted that there are alternative ways of implementing the present invention. Accordingly, the present embodiments are to be considered as illustrative and not restrictive, and the invention is not to be limited to the details given herein, but may be modified within the scope and equivalents of the appended claims. All references and publications cited herein are incorporated by reference in their entirety.

What is claimed is:

1. A method of treating a wrinkle in a subject comprising:
    implanting a hydratable thread into the dermis of a subject in need thereof wherein the thread comprises uncrosslinked hyaluronic acid or salts, hydrates or solvates thereof and crosslinked hyaluronic acid or salts, hydrates or solvates thereof.

2. The method of claim 1 wherein the crosslinked hyaluronic acid is crosslinked with a crosslinker selected from the group consisting of butanediol diglycidyl ether (BDDE), divinyl sulfone (DVS) and 1-ethyl-3-(3-dimethylaminopropyl) carbodiimide hydrochloride (EDC).

3. The method of claim 1 wherein the crosslinked hyaluronic acid is crosslinked with butanediol diglycidyl ether (BDDE).

4. The method of claim 1 further comprising implanting the thread using a needle attached to the thread.

5. The method of claim 4 wherein the implanting comprises
    inserting a distal end of the needle through the skin surface of the subject adjacent to the wrinkle;
    traversing the dermis of the subject under the wrinkle with the needle;
    forcing the needle through the skin surface of the subject; and
    cutting the thread from the needle at the skin surface of the subject.

* * * * *

UNITED STATES PATENT AND TRADEMARK OFFICE
CERTIFICATE OF CORRECTION

PATENT NO. : 9,861,570 B2
APPLICATION NO. : 14/947409
DATED : January 9, 2018
INVENTOR(S) : Geoffrey C. Gurtner et al.

Page 1 of 1

It is certified that error appears in the above-identified patent and that said Letters Patent is hereby corrected as shown below:

On the Title Page

On the Page 5, in Column 2, under "Other Publications", Line 5, delete "Depolyrnerization" and insert -- Depolymerization --, therefor.

On the Page 6, in Column 1, under "Other Publications", Line 46, delete "Microparticies" and insert -- Microparticles --, therefor.

On the Page 6, in Column 1, under "Other Publications", Line 50, delete "Ophthalrnology," and insert -- Ophthalmology, --, therefor.

On the Page 6, in Column 2, under "Other Publications", Line 5, delete "Andrenocorticosteroid" and insert -- Adrenocorticosteroid --, therefor.

On the Page 6, in Column 2, under "Other Publications", Line 63, delete "Add" and insert -- Acid --, therefor.

On the Page 7, in Column 1, under "Other Publications", Line 21, delete "Viscoelstic" and insert -- Viscoelastic --, therefor.

Signed and Sealed this
Twentieth Day of March, 2018

Andrei Iancu
*Director of the United States Patent and Trademark Office*